United States Patent
Aradottir et al.

(10) Patent No.: US 11,295,847 B2
(45) Date of Patent: Apr. 5, 2022

(54) SYSTEMS AND METHODS FOR ADJUSTING BASAL ADMINISTRATION TIMING

(71) Applicant: Novo Nordisk A/S, Bagsvaerd (DK)

(72) Inventors: Tinna Bjoerk Aradottir, Copenhagen (DK); Henrik Bengtsson, Taastrup (DK); Pete Brockmeier, Copenhagen V (DK); Jonas Kildegaard Pedersen, Vaerloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 473 days.

(21) Appl. No.: 16/324,940

(22) PCT Filed: Aug. 14, 2017

(86) PCT No.: PCT/EP2017/070588
§ 371 (c)(1),
(2) Date: Feb. 12, 2019

(87) PCT Pub. No.: WO2018/036854
PCT Pub. Date: Mar. 1, 2018

(65) Prior Publication Data
US 2021/0287775 A1    Sep. 16, 2021

(30) Foreign Application Priority Data
Aug. 26, 2016 (EP) .................... 16185931

(51) Int. Cl.
*G16H 20/17* (2018.01)
*G16H 40/60* (2018.01)

(52) U.S. Cl.
CPC ............ *G16H 20/17* (2018.01); *G16H 40/60* (2018.01)

(58) Field of Classification Search
CPC .................... G06Q 50/22–24; G16H 20/17
See application file for complete search history.

(56) References Cited

U.S. PATENT DOCUMENTS 4,946,679 A * 8/1990 Thys-Jacobs .......... A61K 31/19
424/602
8,732,188 B2  5/2014 Doniger et al.
(Continued)

FOREIGN PATENT DOCUMENTS

| JP | 2010519623 A | 6/2010 |
| WO | 2010091129 A1 | 8/2010 |
| WO | 2015169814 A1 | 11/2015 |

OTHER PUBLICATIONS

Anonymous: "Basal Insulins", Diabetesnet.com, Jul. 29, 2016, XP055347897, Retrieved from the Internet: URL:http://web.archive.org/web/20160729045829/http://www.diabetesnet.com/about-diabetes/insulin/basal-insulins, retrieved on Feb. 20, 2017.
(Continued)

*Primary Examiner* — John A Pauls
(74) *Attorney, Agent, or Firm* — Wesley Nicolas

(57) ABSTRACT

Systems and methods are provided for optimizing basal administration timing in a standing basal insulin regimen of a subject. The regimen specifies a total amount of basal insulin medicament, one or more basal injection event types for a recurring period, and an apportionment of the total amount of medicament between the injection event types. Time stamped glucose measurements of the subject are obtained over a past time course comprising a plurality of instances of the recurring period. When the glucose measurements satisfy a stop condition, a recommended adjustment is determined that comprises a change in the number of injection event types in the regimen and/or a change in the apportionment of insulin medicament between injection event types. The recommended adjustment is communicated to the subject for manual adjustment of the regimen, an
(Continued)

insulin pen charged with delivering the regimen to the subject, or a health care practitioner associated with the subject.

16 Claims, 12 Drawing Sheets

(56) References Cited

U.S. PATENT DOCUMENTS

| | | | | |
|---|---|---|---|---|
| 2007/0249916 | A1* | 10/2007 | Pesach | A61B 5/1455 600/316 |
| 2008/0208027 | A1* | 8/2008 | Heaton | G16H 40/63 600/365 |
| 2008/0319384 | A1* | 12/2008 | Yodfat | A61M 5/14248 604/67 |
| 2009/0271729 | A1* | 10/2009 | Killoren Clark | A61B 5/743 715/771 |
| 2011/0098548 | A1 | 4/2011 | Budiman et al. | |
| 2014/0019396 | A1* | 1/2014 | Carlsgaard | G06N 5/02 706/46 |
| 2016/0074587 | A1* | 3/2016 | Searle | A61M 5/16804 604/189 |
| 2018/0296142 | A1* | 10/2018 | St hl | A61B 5/145 |

OTHER PUBLICATIONS

David Spero: "How Do You Use Basal Insulin?", Diabetes Self-Management, Feb. 4, 2015, pp. 1-7, XP055348101, Retrieved from the Internet: URL:https://www.diabetesselfmanagement.com/blog/use-basal-insuliin/, retrieved on Feb. 21, 2017.

David Spero: "How Do You Use Basal Insulin?", Diabetes Self-Management, Aug. 8, 2016 pp. 1-5, XP055347895, Retrieved from the Internet: URL:https://web.archive.org/web/20160808082441/http:/www.diabetesselfmanagement.com/blog/use-basal-insuliin/, retrieved on Feb. 21, 2017.

* cited by examiner

402 — A device 250 for optimizing basal administration timing in a standing basal insulin regimen is provided. The device comprises one or more processors 274 and a memory 290/192. The memory stores instructions that, when executed by the one or more processors, perform a method.

404 — Obtain a standing basal insulin regimen 206 for the subject. The standing basal insulin regimen specifies (i) a total amount of basal insulin medicament 210 for a recurring period 208, (ii) one or more basal injection event types in a set of basal injection event types for the recurring period, and (iii) a respective apportionment 214 of all or a portion of the total amount of basal insulin medicament between each respective basal injection event type 212 in the one or more basal injection event types.

406 — The set of basal injection event types for the recurring period consists of "morning basal" and "night basal," and the recurring period is a day.

408 — Obtain a first data set 216 comprising a plurality of glucose measurements of the subject taken over a past time course. The past time course comprises a first plurality of instances of a recurring period and, for each respective glucose measurement 218 in the plurality of glucose measurements, a glucose measurement timestamp 220 representing when the respective measurement was made.

410 — Successive measurements in the plurality of glucose measurements in the first data set are autonomously taken from the subject at an interval rate of 5 minutes or less, 3 minutes or less, or 1 minute or less

412 — The past time course is the last week, the last two weeks, or the last month. The method is repeated on a recurring basis over time. The basal insulin medicament consists of a single insulin medicament having a duration of action that is between 12 and 24 hours or a mixture of insulin medicaments that collectively have a duration of action that is between 12 and 24 hours.

414 — Evaluate the plurality of glucose measurements over the past time course using a stop condition 222.

416 — Obtain a third data set 302 from an insulin pen 104 used by the subject to apply the basal insulin regimen. The third data set comprises insulin medicament records. Each respective record 304 in the plurality of medicament records comprises: (i) an insulin medicament injection event 306 including an amount of basal insulin medicament injected 308 into the subject and (ii) a corresponding insulin event electronic timestamp 310 that is automatically generated by the insulin pen upon occurrence of the respective insulin medicament injection event. Use the third data set and the standing basal insulin regimen to determine one or more recurring periods in the past time course that do not comply with the standing basal insulin regimen for the subject. Exclude from the stop condition evaluation those glucose measurements in the one or more recurring periods in the past time course that do not comply with the standing basal insulin regimen.

418 — When the stop condition is satisfied, determine a recommended adjustment comprising a change in the number of basal injection event types in the standing basal insulin regimen and/or a change in the respective apportionment of all or a portion of the total amount of basal insulin medicament between each respective basal injection event type in the one or more basal injection event types.

420 — The standing basal insulin regimen specifies a single basal injection event type for the recurring period. The evaluating the glucose measurements over the past time course using the stop condition comprises: obtaining fasting events in the past time course. Each fasting event 226 is associated with a different instance of the recurring period in the plurality of instances of the recurring period. For each respective fasting event in the one or more fasting events, there is compared (i) one or more first glucose measurements of the subject in the first data set occurring at a first time slot that is a first predetermined amount of time prior to a beginning of the respective fasting event to (ii) one or more second glucose measurements of the subject in the first data set occurring at a second time slot that is at a predetermined point within or after the respective fasting event, thereby obtaining one or more comparisons. The stop condition is satisfied when the comparisons indicate that the respective one or more first glucose measurements deviate from the corresponding respective one or more second glucose measurements by more than a threshold amount. The recommended adjustment increases the number of basal injection event types to two and apportions the total amount of basal insulin medicament between the two basal injection event types.

Fig. 4B

SYSTEMS AND METHODS FOR ADJUSTING BASAL ADMINISTRATION TIMING

CROSS-REFERENCE TO RELATED APPLICATIONS

This application is a 35 U.S.C. § 371 National Stage application of International Application PCT/EP2017/070588 (published as WO 2018/036854), filed Aug. 14, 2017, which claims priority to European Patent Application 16185931.9, filed Aug. 26, 2016, the contents of all above-named applications are incorporated herein by reference.

TECHNICAL FIELD

The present disclosure relates generally to systems and methods for optimizing basal administration timing in a standing insulin regimen for a subject that includes a basal insulin medicament.

BACKGROUND

Type 2 diabetes mellitus is characterized by progressive disruption of normal physiologic insulin secretion. In healthy individuals, basal insulin secretion by pancreatic β cells occurs continuously to maintain steady glucose levels for extended periods between meals. Also in healthy individuals, there is prandial secretion in which insulin is rapidly released in an initial first-phase spike in response to a meal, followed by prolonged insulin secretion that returns to basal levels after 2-3 hours.

Insulin is a hormone that binds to insulin receptors to lower blood glucose by facilitating cellular uptake of glucose, amino acids, and fatty acids into skeletal muscle and fat and by inhibiting the output of glucose from the liver. In normal healthy individuals, physiologic basal and prandial insulin secretions maintain euglycemia, which affects fasting plasma glucose and postprandial plasma glucose concentrations. Basal and prandial insulin secretion is impaired in Type 2 diabetes and early post-meal response is absent. To address these adverse events, subjects with Type 2 diabetes are provided with insulin medicament treatment regimens. Subjects with Type 1 diabetes are also provided with insulin medicament treatment regimens. The goal of these insulin medicament treatment regimens is to maintain a desired fasting blood glucose target level that will minimize estimated risk of hypo- and hyper-glycaemia.

Traditional insulin medicament delivery systems have included the use of pump systems that provide a frequent recurrent dosage of insulin medicament. More recently, additional types of delivery systems have been developed, such as insulin pens, which can be used to self-administer insulin medicament treatment regimens in the form of less frequent insulin medicament injections. A common approach to diabetes treatment using such delivery systems is to inject a long acting insulin medicament (basal) dosage in accordance with the standing insulin regimen to maintain glycaemic control independent of meal events. However, the optimal delivery of such long acting insulin medicament (basal) dosage is subject specific. In some subjects it is best to split the basal dosage into two or more dosages per day in order to best maintain glycaemic control whereas in other subjects it is best to administer the basal dosage at a single time each day.

In practice, a health care practitioner typically determines a total daily amount of basal insulin medicament a subject should take. Moreover, the health care practitioner determines, based on available medical data about the subject, whether this daily basal insulin medicament allotment should be administered as a single injection event, or in multiple injection events over the course of the day. The determination made by the health care practitioner is formalized as a standing basal insulin regimen which the subject is directed to adhere to until the next visit by the subject to the health care practitioner. The drawback with this conventional practice is twofold. First, the health care practitioner conventionally uses limited data to draw upon in order to establish the standing basal insulin regimen. Thus, the standing basal insulin regimen risks not being optimal for a given subject due to the limited data used to formalize the standing basal insulin regimen. Second, subjects are not able to visit the health care practitioner frequently enough to truly optimize the standing basal insulin regimen. For instance, the optimal standing basal insulin regimen may shift between health care practitioner visits due to health events that occur between visits. These shifts in the optimal standing basal insulin regimen are not discovered until the next health care practitioner visit. These drawbacks with conventional practice result in some subjects administering the basal insulin medicament as more than one dose over the course of the day when, in fact, it would be better for such subjects to administer the basal insulin medicament as a single dose. Conversely, other subjects that are directed to administer their basal insulin medicament in a single injection event each day are better served, in fact, if they were to break up the daily basal insulin medicament dosage into smaller dosages that are injected at multiple times during the day.

United States Patent Publication No. 20110098548 entitled "Methods for Modeling Insulin Therapy Requirements" to Abbott Diabetes Care Inc. discloses a system for processing diabetes related information, including glucose information, for predicting future glucose levels as a function of glucose data, carbohydrate intake, insulin delivery history and exercise history and subsequently providing recommendations related to the predicted future glucose levels. However, the 20110098548 provides no teaching on how to apportion a recurring basal insulin medicament dosage into a discrete set of injection events (e.g., a single injection event or multiple injection events) in order to minimize glycaemic risk.

International Patent Publication WO2015/169814 entitled "Insulin Dosage Proposal System" to Joanneum Res Forschungs GMBH discloses systems and methods for determining a proposal for an insulin dosage that includes doses and assigned times of the day according to which insulin is to be administered to a diabetes patient. However, like the 20110098458 publication, the WO2015/169814 publication provides no teaching on how to apportion a recurring basal insulin medicament dosage into a discrete set of injection events (e.g., a single injection event or multiple injection events) in order to minimize glycaemic risk.

International Patent Publication WO 2010/091129 entitled "Multi-Function Analyte Test Device and Methods Therefore" to Abbott Diabetes Care discloses a health monitoring device that may include instruction to perform a long-acting medication dosage calculation function. A long-acting medication may be a medication wherein a single dose may last for up to 12 hours, 24 hours, or longer. The instructions for a long-acting medication dosage calculation function may be in the form of software stored on the memory device and executed by the processor of the health monitor device. In one aspect, the long-acting medication dosage calculation function may be an algorithm based on the current concentration of an analyte of a patient, wherein the long-acting medication dosage calculation function compares the current analyte concentration value to a predetermined threshold, which may be based on clinically determined threshold levels for a particular analyte, or may be tailored for individual patients by a doctor or other treating professional. If the current analyte concentration is above the predetermined threshold, the long-acting medication dosage calculation function may use the current analyte concentration value to calculate a recommended dosage of a long-acting medication. Once calculated, the recommended medication dosage may be displayed on the display unit of the health monitor device. However, the WO 2010/091129 publication provides no teaching on how to apportion a recurring basal insulin medicament dosage into a discrete set of injection events (e.g., a single injection event or multiple injection events) in order to minimize glycaemic risk.

Given the above background, what is needed in the art are systems and methods for optimizing basal administration timing in order to minimize glycaemic risk and for communicating this information to subjects so that the basal insulin medicament is administered with insulin pens in accordance with the optimal basal administration timing.

SUMMARY

The present disclosure addresses the need in the art for optimizing basal administration timing in a standing basal insulin regimen of a subject specifying a total amount of basal insulin medicament, one or more basal injection event types for a recurring period (e.g., a day), and an apportionment of the total amount of medicament between the injection event types in the recurring period. Timestamped glucose measurements of the subject are obtained over a past time course. This past time course comprises a plurality of instances of the recurring period (e.g., several days, where the recurring period is a single day).

When the glucose measurements satisfy a stop condition, a recommended adjustment is determined. This recommended adjustment comprises a change in the number of injection event types in the standing basal insulin regimen and/or a change in the apportionment of insulin medicament between injection event types in the recurring period. The recommended adjustment is communicated to the subject for manual adjustment of the standing basal insulin regimen, an insulin pen charged with delivering the standing basal insulin regimen to the subject, or a health care practitioner associated with the subject.

As such, one aspect of the present disclosure provides a device for optimizing basal administration timing in a standing basal insulin regimen for a subject. The device comprises one or more processors and a memory. The memory stores instructions that, when executed by the one or more processors, performs a method. In the method, the standing basal insulin regimen for the subject is obtained. The standing basal insulin regimen specifies (i) a total amount of basal insulin medicament for a recurring period (e.g., a one day period, a two day period, etc.), (ii) one or more basal injection event types in a set of basal injection event types for the recurring period, and (iii) a respective apportionment of the total amount of basal insulin medicament between each respective basal injection event type in the one or more basal injection event types in a given recurring period.

In the method, a first data set is also obtained. The first data set comprises a plurality of glucose measurements of the subject over a past time course. The past time course comprises a first plurality of instances of the recurring period. For instance, if the recurring period is a day, the past time course comprises several days. For each respective glucose measurement in the plurality of glucose measurements, there is a glucose measurement timestamp representing when the respective measurement was made.

In the method, the plurality of glucose measurements over the past time course is evaluated using a stop condition. When the stop condition is satisfied, the method further comprises determining a recommended adjustment to the standing basal insulin regimen. As such, the recommended adjustment comprises a change in the number of basal injection event types in the standing basal insulin regimen and/or a change in the respective apportionment of the total amount of basal insulin medicament between each respective basal injection event type in the one or more basal injection event types.

The recommended adjustment is communicated to: (i) the subject for manual adjustment of the basal insulin regimen, (ii) an insulin pen charged with delivering the standing basal insulin regimen to the subject, or (iii) a health care practitioner associated with the subject.

In other words the device communicates an apportionment of the total basal insulin between one or more basal injection event types, without increasing the amount of basal insulin, i.e., the total basal insulin. The stop condition indicates that data based on the first data set has been analysed and when the stop condition is evaluated against the analysed data, a satisfied stop condition indicates that the apportionment and/or the number of basal injection event types should be changed. The analysis and the stop condition can be based directly on the measurements or on predictions based on the measurements. The stop condition can be a comparison of glucose measurements related to a fasting period, or the stop condition can be an indication on that a change in apportionment or number of basal injection event types will affect the glycaemic risk to the better or worse.

In some embodiments, the standing basal insulin regimen specifies a single basal injection event type for the recurring period and the evaluating the plurality of glucose measurements over the past time course using the stop condition comprises obtaining one or more fasting events in the past time course. Each such fasting event is associated with a different instance of the recurring period in the first plurality of instances of the recurring period. For instance, if the recurring period is a day, each respective fasting period is associated with a different day in the past time course. That is, if the recurring period is one day, an example of a "different instance" of the recurring period would be a particular day, such as Tuesday, May 5.

For each respective fasting event in the one or more fasting events, a comparison is made between (i) one or more first glucose measurements of the subject in the first data set occurring at a first time slot that is a first predetermined amount of time prior to a beginning of the respective fasting event and (ii) one or more second glucose measurements of the subject in the first data set occurring at a second time slot that is at a predetermined point within or after the respective fasting event. In this way, one or more comparisons are obtained. In such embodiments, the stop condition is satisfied when the one or more comparisons indicate that the respective one or more first glucose measurements deviate from the corresponding respective one or more second glucose measurements by more than a threshold amount. In this case, the recommended adjustment is to increase the number of basal injection event types to two basal injection event types and to apportion the total amount of basal insulin medicament between the two basal injection event types.

In a further or alternative aspect, the standing basal insulin regimen specifies a single basal injection event type for the recurring period, and the evaluating the plurality of glucose measurements over the past time course using the stop condition comprises:

obtaining a plurality of fasting events in the past time course, wherein each fasting event is associated with a different instance of the recurring period in the first plurality of instances of the recurring period, obtaining, for each respective fasting event in the plurality of fasting events, (i) a first glucose measurements of the subject in the first data set occurring at a first time slot that is a first predetermined amount of time prior to a beginning of the respective fasting, and (ii) a second glucose measurements of the subject in the first data set occurring at a second time slot that is at a predetermined point within or after the respective fasting event, obtaining a first measure of central tendency of the first glucose measurement of each fasting event in the plurality of fasting event, and a second measure of central tendency of the second glucose measurement of each fasting in the plurality of fasting events, and comparing the first measure of central tendency to the second measure of central tendency, and thereby obtaining a comparison, wherein, the stop condition is satisfied when the comparison indicate that the respective first measure of central tendency deviate from the second measure of central tendency by more than a threshold amount, and the recommended adjustment is to increase the number of basal injection event types to two basal injection event types and to apportion the total amount of basal insulin medicament between the two basal injection event types.

In some such embodiments, the obtaining the one or more fasting events comprises identifying a first fasting event in a first recurring period in the first plurality of recurring periods by computing a moving period of variance $\sigma_k^2$ across the plurality of glucose measurements, where $$\sigma_k^2 = \left(\frac{1}{M} \sum_{i=k-M+1}^{k} (G_i - \overline{G})\right)^2$$

where $G_i$ is the $i^{th}$ glucose measurement in a portion k of the plurality of glucose measurements, M is a number of glucose measurements in the plurality of glucose measurements and represents the past time course, $\overline{G}$ is the mean of the glucose measurements selected from the plurality of glucose measurements, and k is within the first recurring period. In such embodiments, the first fasting event is associated with a region of minimum variance $$\min_k \sigma_k^2$$

within the first recurring period. In alternative embodiments, the obtaining the one or more fasting events comprises receiving an indication of each fasting event in the one or more fasting events from the subject. In still further alternative embodiments, the obtaining the one or more fasting events comprises receiving a second data set from a wearable device worn by the subject, and the second data set indicates a physiological metric of the subject during the time course that is indicative of the one or more fasting events.

In some embodiments, the method further comprises obtaining a third data set from an insulin pen used by the subject to apply the standing basal insulin regimen. The third data set comprises a plurality of insulin medicament records. Each respective insulin medicament record in the plurality of medicament records comprises: (i) a respective insulin medicament injection event including an amount of basal insulin medicament injected into the subject and (ii) a corresponding insulin event electronic timestamp that is automatically generated by the insulin pen upon occurrence of the respective insulin medicament injection event. In the method, the third data set and the standing basal insulin regimen is used to determine one or more recurring periods in the past time course that do not comply with the standing basal insulin regimen for the subject. The glucose measurements taken during such recurring periods that do not comply with the standing basal insulin regimen for the subject are excluded from the stop condition evaluation.

In some embodiments, the set of basal injection event types for the recurring period consists of "morning basal" and "night basal." Further, the standing basal insulin regimen specifies a single basal injection event type for the recurring period. Further still, the recommended adjustment is to add the "night basal" basal injection event type to the standing basal insulin regimen and to apportion the total amount of basal insulin medicament between the "night basal" basal injection event type and the "morning basal" basal injection event type.

In some embodiments, the method further comprises obtaining a second data set from an insulin pen used by the subject to apply the standing basal insulin regimen. The second data set comprises a plurality of insulin medicament records over the past time course.

Each insulin medicament record in the plurality of medicament records comprises: (i) a respective insulin medicament injection event representing an insulin medicament injection of the basal insulin medicament into the subject using the insulin pen and (ii) a corresponding electronic timestamp that is automatically generated by the insulin pen upon occurrence of the respective insulin medicament injection event. The first data set and the second data set are used to simulate a glucose concentration of the subject over a future time course a plurality of times, thereby computing a plurality of simulations of the glucose concentration of the subject over the future time course. Each respective simulation in the plurality of simulations is associated with a different apportionment of the total amount of basal insulin medicament across the set of basal injection event types. In such embodiments, the evaluating the plurality of glucose measurements over the past time course using the stop condition comprises evaluating the glucose concentration of the subject across the future time course in each respective simulation in the plurality of simulations by calculating a glycaemic risk metric for each simulation. The stop condition is satisfied when a first simulation in the plurality of simulations minimizes the glycaemic risk metric, by more than a threshold amount as compared to one of (i) a reference simulation of the glucose concentration of the subject over the future time course based upon the apportionment of the total amount of basal insulin medicament across the set of basal injection event types specified in the standing basal insulin regimen and (ii) the glucose concentration of the subject across the first data set. In such embodiments, the apportionment of the total amount of basal insulin medicament across the set of basal injection event types in the first simulation is different than that of the standing basal insulin regimen. In some such embodiments, the glycaemic risk metric comprises: (i) a total glucose level variability observed across the respective simulation, (ii) a variability in a plurality of fasting glucose levels calculated across the respective simulation, (iii) a percentage of time that a total glucose level exceeds a first threshold value or falls below a second threshold value across the respective simulation, or (iv) a percentage of time that an HbA1c level exceeds a third threshold value or falls below a fourth threshold value across the respective simulation.

In some such embodiments, a meal record data set is obtained. The meal record data set comprises a plurality of meal records over the past time course for the subject. Each respective meal record in the meal record data set comprises: (i) a carbohydrate intake event and (ii) a corresponding electronic carbohydrate timestamp of when the carbohydrate intake event occurred. In such embodiments, the using the first data set and the second data set to simulate a glucose concentration of the subject over a future time course a plurality of times comprises using the first data set, the second data set, and the meal record data set to simulate a glucose concentration of the subject over the future time course the plurality of times.

In some such embodiments, the method further comprises obtaining a fourth data set comprising physical exertion of the subject over the past time course. In such embodiments, the using the first data set and the second data set to simulate a glucose concentration of the subject over a future time course a plurality of times comprises using the first data set, the second data set, the third data set and the fourth data set to simulate a glucose concentration of the subject over the future time course the plurality of times.

In some embodiments, the set of basal injection event types for the recurring period consists of "morning basal" and "night basal" and the recurring period is a day.

In some embodiments, successive measurements in the plurality of glucose measurements in the first data set are autonomously taken from the subject at an interval rate of 5 minutes or less, 3 minutes or less, or 1 minute or less.

In some embodiments, the past time course is the last week, the last two weeks, or the last month and the method is repeated on a recurring basis over time. Further, the basal insulin medicament consists of a single insulin medicament having a duration of action that is between 12 and 24 hours or a mixture of insulin medicaments that collectively have a duration of action that is between 12 and 24 hours.

Another aspect of the present disclosure provides a method for a method for optimizing basal administration timing in a standing basal insulin regimen for a subject. The method comprises obtaining the standing basal insulin regimen for the subject. The standing basal insulin regimen specifies (i) a total amount of basal insulin medicament for a recurring period, (ii) one or more basal injection event types in a set of basal injection event types for the recurring period, and (iii) a respective apportionment of the total amount of basal insulin medicament between each respective basal injection event type in the one or more basal injection event types. In the method, a first data set is obtained. The first data set comprises a plurality of glucose measurements of the subject over a past time course. The past time course comprises a first plurality of instances of the recurring period. The first data set further comprises, for each respective glucose measurement in the plurality of glucose measurements, a timestamp representing when the respective measurement was made. In the methods, the plurality of glucose measurements are evaluated over the past time course using a stop condition. When the stop condition is satisfied, the method further comprises determining a recommended adjustment comprising a change in the number of basal injection event types in the standing basal insulin regimen and/or a change in the respective apportionment of all or a portion of the total amount of basal insulin medicament between each respective basal injection event type in the one or more periodic injection event types. The recommended adjustment is communicated to: (i) the subject for manual adjustment of the basal insulin regimen, (ii) an insulin pen charged with delivering the standing basal insulin regimen to the subject, or (iii) a health care practitioner associated with the subject.

In a further aspect is provided a computer program comprising instructions that, when executed by one or more processors, perform the method of:
obtaining the standing basal insulin regimen for the subject, wherein the standing basal insulin regimen specifies (i) a total amount of basal insulin medicament for a recurring period, (ii) one or more basal injection event types in a set of basal injection event types for the recurring period, and (iii) a respective apportionment of the total amount of basal insulin medicament between each respective basal injection event type in the one or more basal injection event types;
obtaining a first data set, the first data set comprising a plurality of glucose measurements of the subject over a past time course, the past time course comprising a first plurality of instances of the recurring period and, for each respective glucose measurement in the plurality of glucose measurements, a glucose measurement timestamp representing when the respective measurement was made;
evaluating the plurality of glucose measurements over the past time course using a stop condition, wherein, when the stop condition is satisfied, the method further comprises:
determining a recommended adjustment comprising a change in the number of basal injection event types in the standing basal insulin regimen and/or a change in the respective apportionment of the total amount of basal insulin medicament between each respective basal injection event type in the one or more basal injection event types; and
communicating the recommended adjustment to: (i) the subject for manual adjustment of the standing basal insulin regimen, (ii) an insulin pen charged with delivering the standing basal insulin regimen to the subject, or (iii) a health care practitioner associated with the subject.

In a further aspect is provided, a computer-readable data carrier having stored thereon the computer program as described above.

BRIEF DESCRIPTION OF THE DRAWINGS

FIGS. 4A, 4B, 4C, 4D, and 4E collectively provide a flow chart of processes and features of a device for optimizing basal administration timing in a standing basal insulin regimen for a subject, where optional elements of the flow chart are indicated by dashed boxes, in accordance with various embodiments of the present disclosure.

Like reference numerals refer to corresponding parts throughout the several views of the drawings.

DETAILED DESCRIPTION

Figure 1:
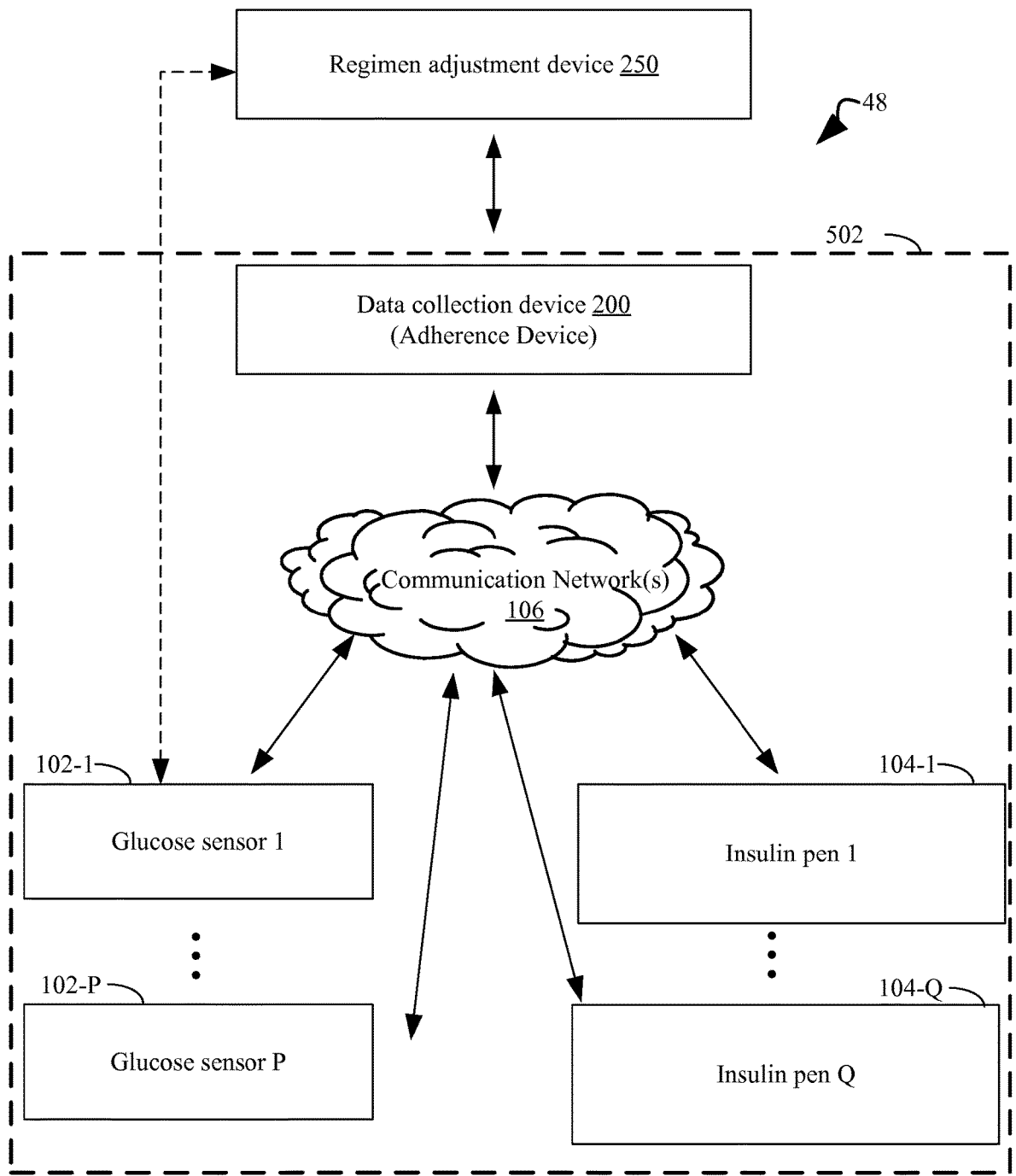
FIG. 1 illustrates an exemplary system topology that includes a regimen adjustment device for optimizing basal administration timing in a standing basal insulin regimen for a subject, a data collection device for collecting subject data, one or more glucose sensors that measure glucose data from the subject, and one or more insulin pens that are used by the subject to inject insulin medicaments in accordance with the standing basal insulin regimen, where the above-identified components are interconnected, optionally through a communications network, in accordance with an embodiment of the present disclosure.
Figure 5:
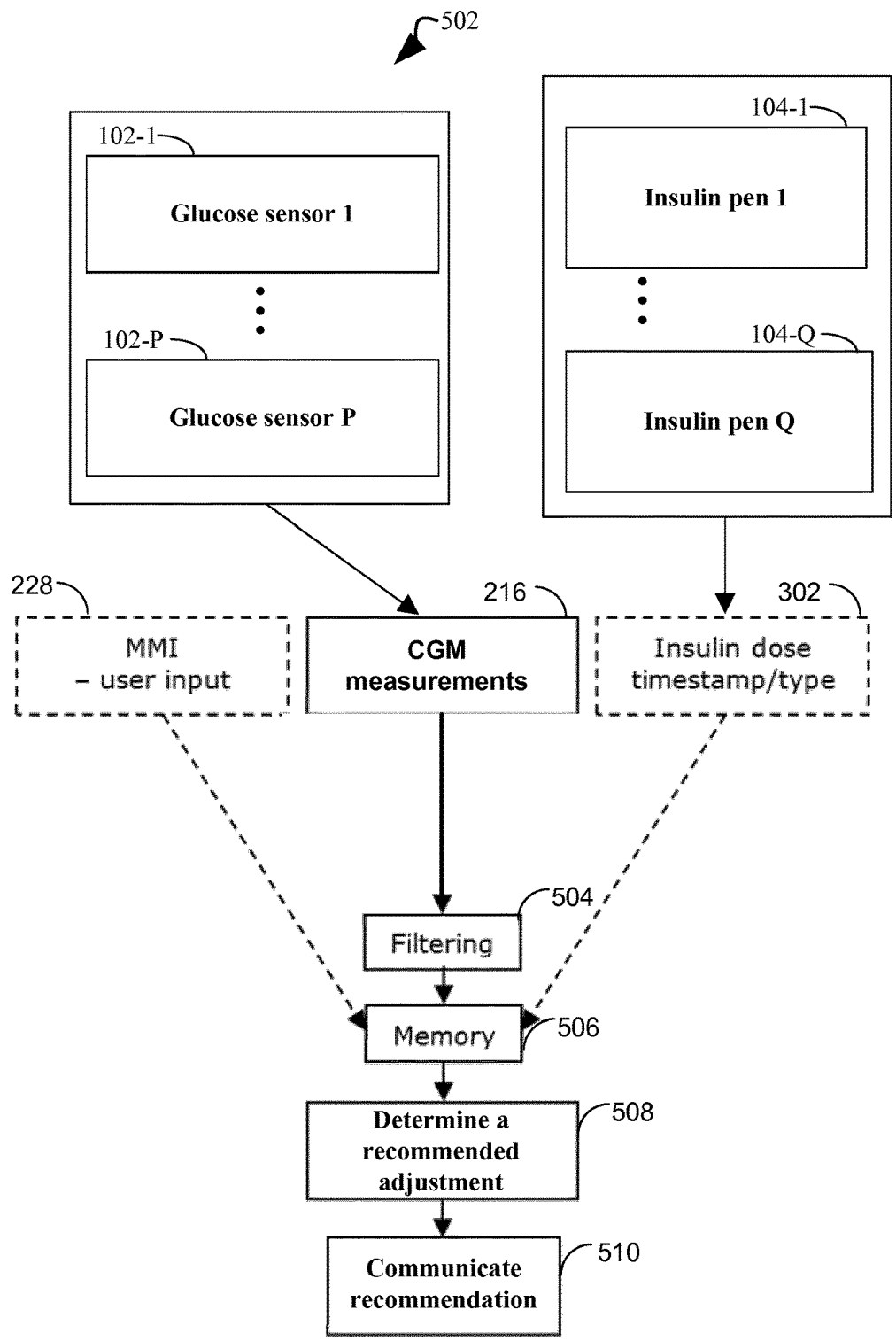
FIG. 5 illustrates an example integrated system of connected insulin pen(s), continuous glucose monitor(s), memory and a processor for optimizing basal administration timing in a standing basal insulin regimen for a subject in accordance with an embodiment of the present disclosure.

The present disclosure provides systems and methods for optimizing basal administration timing in a standing basal insulin regimen for a subject. FIG. 1 illustrates an example of an integrated system 502 for optimizing basal administration timing in a standing basal insulin regimen for a subject, and FIG. 5 provides more details of such a system 502. The integrated system 502 includes one or more connected insulin pens 104, one or more glucose monitors 102, memory 506, and a processor (not shown) for adjusting a basal/bolus ratio in a standing insulin regimen for a subject. In some embodiments, a glucose monitor 102 is a continuous glucose monitor. In FIG. 5, optional physiological measurements 230 in the form of a second data set 228, continuous glucose measurements in the form of a first data set 216, and optional insulin dose/timestamp/type data in the form of a third data set 302 are filtered 504, stored in memory 192/290 (step 506) and a determination on whether to make a recommended adjustment to the standing insulin regimen 206 is made at step 508. When a recommended adjustment to the standing insulin regimen is made it is then communicated to a subject 510

With the integrated system, the basal administration timing in a standing basal insulin regimen is optimized for a subject, where the standing basal insulin regimen specifies (i) a total amount of basal insulin medicament for a recurring period (e.g., a day), (ii) one or more basal injection event types in a set of basal injection event types (e.g., "morning basal," "evening basal") for the recurring period, and (iii) a respective apportionment of the total amount of basal insulin medicament between each respective basal injection event type in the one or more basal injection event types. Time-stamped glucose measurements of the subject are obtained over a past time course comprising a plurality of instances of the recurring period. When the glucose measurements satisfy a stop condition, a recommended adjustment is determined that comprises a change in the number of injection event types in the standing basal insulin regimen and/or a change in the apportionment of insulin medicament between injection event types. The recommended adjustment is communicated to the subject for manual adjustment of the standing basal insulin regimen, an insulin pen charged with delivering the standing basal insulin regimen to the subject, or a health care practitioner associated with the subject.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein. By the term "insulin pen," is meant an injection device suitable for applying discrete doses of insulin, where the injection device is adapted for logging and communicating dose related data. By the term "injection event," is meant the use of an insulin pen to apply a discrete dose of an insulin medicament.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

A detailed description of a system 48 for optimizing basal administration timing in a standing basal insulin regimen for a subject in accordance with the present disclosure is described in conjunction with FIGS. 1, 2, 3, and 5. As such, FIGS. 1, 2, 3, and 5 collectively illustrate the topology of the system in accordance with the present disclosure. In the topology, there is a regimen adjustment device for optimizing basal administration timing in a standing basal insulin regimen for a subject ("regimen adjustment device 250") (FIGS. 1, 2, and 3), a device for data collection ("data collection device 200"), one or more glucose sensors 102 associated with the subject (FIGS. 1 and 5), and one or more insulin pens 104 for injecting insulin medicaments into the subject (FIGS. 1 and 5). Throughout the present disclosure, the data collection device 200 and the regimen adjustment device 250 will be referenced as separate devices solely for purposes of clarity. That is, the disclosed functionality of the data collection device 200 and the disclosed functionality of the regimen adjustment device 250 are contained in separate devices as illustrated in FIG. 1. However, it will be appreciated that, in fact, in some embodiments, the disclosed functionality of the data collection device 200 and the disclosed functionality of the regimen adjustment device 250 are contained in a single device. In some embodiments, the disclosed functionality of the data collection device 200 and/or the disclosed functionality of the regimen adjustment device 250 are contained in a single device and this single device is a glucose monitor 102 or an insulin pen 104.

Referring to FIG. 1, the regimen adjustment device 250 optimizes the basal administration timing in a standing basal insulin regimen for a subject. To do this, the data collection device 200, which is in electrical communication with the regimen adjustment device 250, receives glucose measurements originating from one or more glucose sensors 102 attached to a subject on an ongoing basis. In some embodiments, the data collection device 200 also receives insulin medicament injection data from one or more insulin pens 104 used by the subject to inject insulin medicaments. In some embodiments, the data collection device 200 receives such data directly from the glucose sensor(s) 102 and insulin pens 104 used by the subject. For instance, in some embodiments the data collection device 200 receives this data wirelessly through radio-frequency signals. In some embodiments such signals are in accordance with an 802.11 (WiFi), Bluetooth, or ZigBee standard. In some embodiments, the data collection device 200 receives such data directly, analyzes the data, and passes the analyzed data to the regimen adjustment device 250. In some embodiments, a glucose sensor 102 and/or insulin pen 104 includes an RFID tag and communicates to the data collection device 200 and/or the regimen adjustment device 250 using RFID communication. In some embodiments, referring to FIG. 2, the data collection device 200 also obtains or receives physiological measurements 232 of the subject (e.g., from wearable physiological measurement devices, from measurement devices within the data collection device 200 such as a magnetometer or a thermostat, etc.).

In some embodiments, the data collection device 200 and/or the regimen adjustment device 250 is not proximate to the subject and/or does not have wireless capabilities or such wireless capabilities are not used for the purpose of acquiring glucose data, insulin medicament injection data, and/or physiological measurement data. In such embodiments, a communication network 106 may be used to communicate glucose measurements from the glucose sensor(s) 102 to the data collection device 200 and/or the regimen adjustment device 250, insulin medicament injection data from the one or more insulin pens 104 to the data collection device 200 and/or the regimen adjustment device 250, and/or physiological measurement data from one or more physiological measurement devices (not shown) to the data collection device 200 and/or the regimen adjustment device 250.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

In some embodiments, there is a single glucose sensor 102 attached to the subject and the data collection device 200 and/or the regimen adjustment device 250 is part of the glucose sensor 102. That is, in some embodiments, the data collection device 200 and/or the regimen adjustment device 250 and the glucose sensor 102 are a single device.

In some embodiments, the data collection device 200 and/or the regimen adjustment device 250 is part of an insulin pen. That is, in some embodiments, the data collection device 200 and/or the regimen adjustment device 250 and an insulin pen 104 are a single device.

Of course, other topologies of the system 48 are possible. For instance, rather than relying on a communications network 106, the one or more glucose sensors 102 and the one or more insulin pens 104 may wirelessly transmit information directly to the data collection device 200 and/or regimen adjustment device 250. Further, the data collection device 200 and/or the regimen adjustment device 250 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Figure 2:
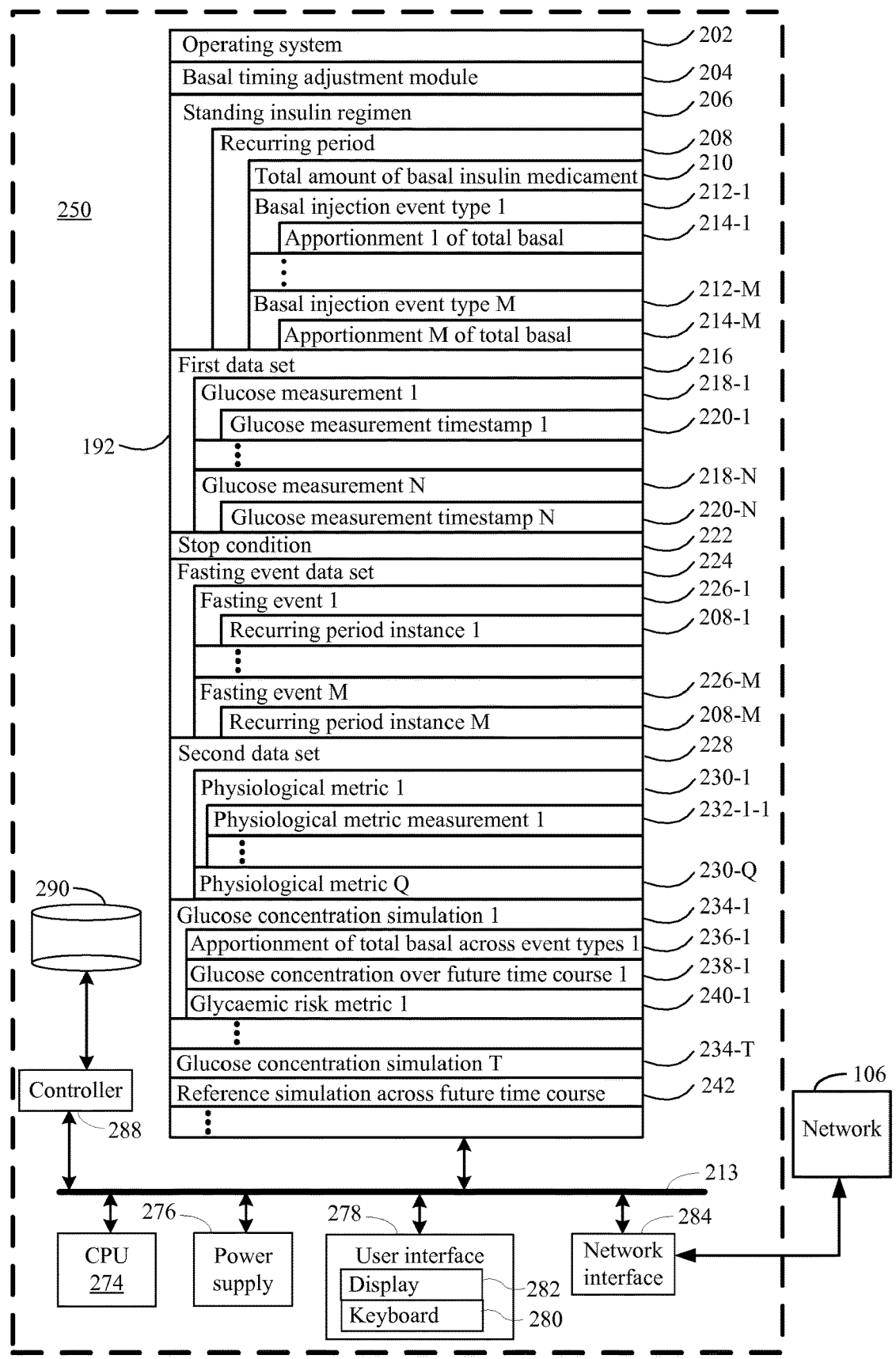
FIG. 2 illustrates a device for optimizing basal administration timing in a standing basal insulin regimen for a subject in accordance with an embodiment of the present disclosure.

Referring to FIG. 2, in typical embodiments, the regimen adjustment device 250 comprises one or more computers. For purposes of illustration in FIG. 2, the regimen adjustment device 250 is represented as a single computer that includes all of the functionality for optimizing basal administration timing in a standing basal insulin regimen for a subject. However, the disclosure is not so limited. In some embodiments, the functionality for optimizing basal administration timing in a standing basal insulin regimen for a subject is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 2 with the foregoing in mind, an exemplary regimen adjustment device 250 for optimizing basal administration timing in a standing basal insulin regimen for a subject comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the regimen adjustment device 250 but that can be electronically accessed by the regimen adjustment device 250 over an Internet, intranet, or other form of network or electronic cable (illustrated as element 106 in FIG. 2) using network interface 284.

In some embodiments, the memory 192 of the regimen adjustment device 250 for optimizing basal administration timing in a standing basal insulin regimen for a subject stores:

an operating system 202 that includes procedures for handling various basic system services;

a basal timing adjustment module 204;

a standing insulin regimen 206 for the subject, the standing insulin regimen comprising a recurring period 208 and, for each instance of the recurring period, a total amount of basal insulin medicament 210 that is to be administered in the recurring period through execution of one or more basal injection event types, where each basal injection event type 212 is associated with a respective apportionment 214 of the total amount of basal insulin medicament;

a first data set 216, the first data set comprising a plurality of glucose measurements of the subject over a past time course, and for each respective glucose measurement 218 in the plurality of glucose measurements, a glucose measurement timestamp 220 representing when the respective glucose measurement was made;

a stop condition 222 that is used to evaluation the plurality of glucose measurements of the subject over the past time course;

a fasting event data set 224 comprising a plurality of fasting events that occur in the past time course encompassed by the first data set, each such fasting event 226 associated with a different recurring period instance 208 within the past time course;

an optional second data set 228 that comprises one or more physiological metrics and, for each respective physiological metric 230 in the one or more physiological metrics, one or more physiological metric measurements 232 of the subject;

a plurality of simulations of the glucose concentration of the subject over a future time course, each respective glucose concentration simulation 234 based upon the first data set and the second data set and associated with a different apportionment 236 of the total amount of basal insulin medicament across the set of basal injection event types thereby providing a glucose concentration over the future time course 238 and an associated glycaemic risk metric 240; and an optional reference glucose simulation 242 across the future time course based upon the apportionment 236 of the total amount of basal insulin medicament as set forth in the standing insulin regimen 206.

In some embodiments, the physiological metric measurement 233 is body temperature of the subject. In some embodiments, the physiological metric measurement 233 is a measurement of activity of the subject. In some embodiments, these physiological metric measurements serve as an additional input for optimizing basal administration timing in a standing basal insulin regimen for a subject. In some embodiments, the optional accelerometer 317, optional GPS 319, and/or magnetometer (not shown) of the regimen adjustment device 250 or such components optionally within the one or more glucose monitors 102 and/or the one or more insulin pens 104 is used to acquire such physiological metric measurements 232.

In some embodiments, the basal timing adjustment module 204 is accessible within any browser (phone, tablet, laptop/desktop). In some embodiments, the basal timing adjustment module 204 runs on native device frameworks, and is available for download onto the regimen adjustment device 250 running an operating system 202 such as Android or iOS.

In some implementations, one or more of the above identified data elements or modules of the regimen adjustment device 250 for optimizing basal administration timing in a standing basal insulin regimen for a subject are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments, the memory 192 and/or 290 stores additional modules and data structures not described above.

In some embodiments, a regimen adjustment device 250 for optimizing basal administration timing in a standing basal insulin regimen for a subject is a smart phone (e.g., an iPHONE), laptop, tablet computer, desktop computer, or other form of electronic device (e.g., a gaming console). In some embodiments, the regimen adjustment device 250 is not mobile. In some embodiments, the regimen adjustment device 250 is mobile.

Figure 3:
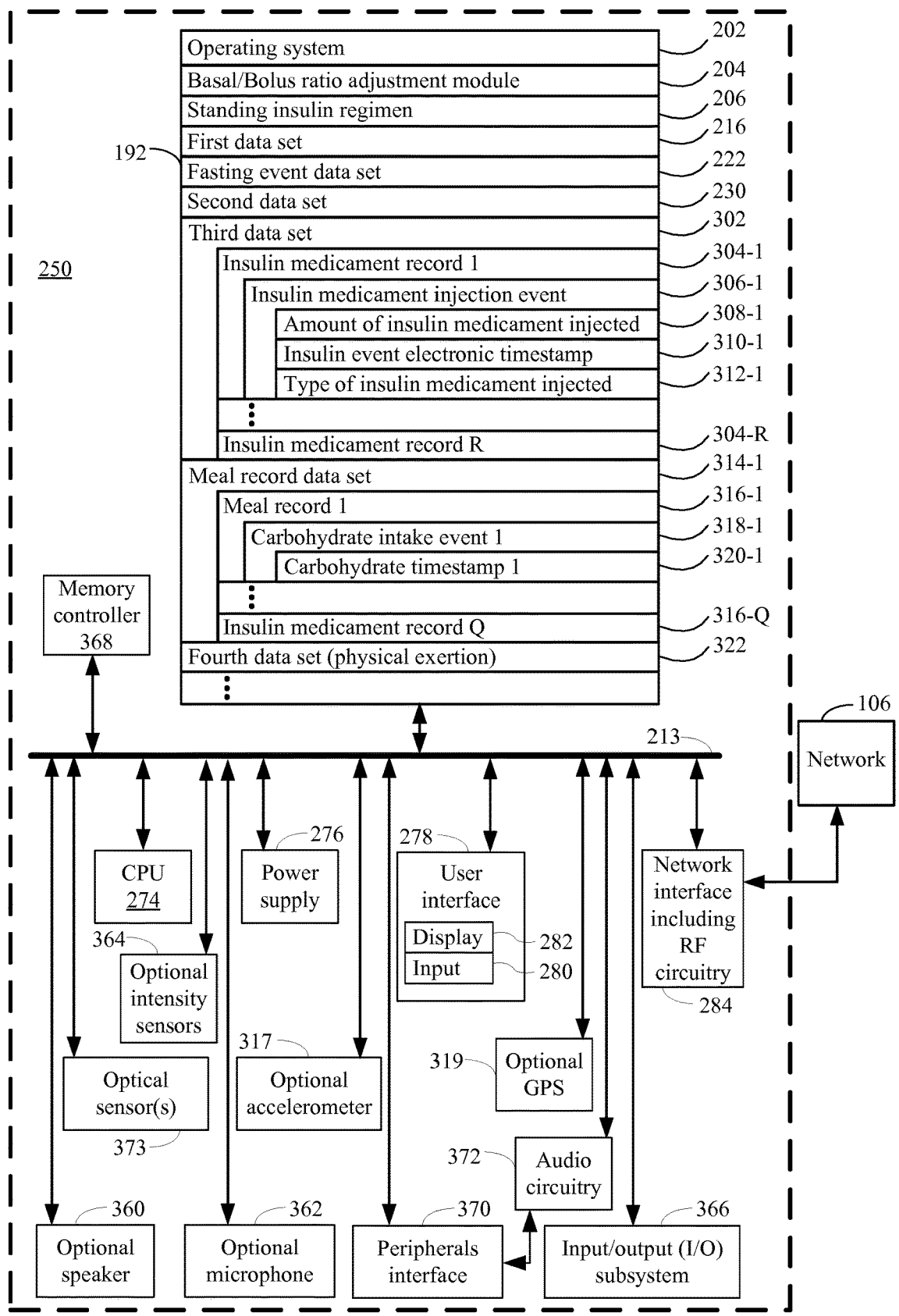
FIG. 3 illustrates a device for optimizing basal administration timing in a standing basal insulin regimen for a subject in accordance with another embodiment of the present disclosure.

FIG. 3 provides a further description of a specific embodiment of a regimen adjustment device 250 in accordance with the instant disclosure. The regimen adjustment device 250 illustrated in FIG. 3 has one or more processing units (CPU's) 274, peripherals interface 370, memory controller 368, a network or other communications interface 284, a memory 192 (e.g., random access memory), a user interface 278, the user interface 278 including a display 282 and input 280 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the regimen adjustment device 250 (e.g., a touch-sensitive surface such as a touch-sensitive display system 282 of the regimen adjustment device 250), an optional input/output (I/O) subsystem 366, one or more optional optical sensors 373, one or more communication busses 213 for interconnecting the aforementioned components, and a power supply 276 for powering the aforementioned components.

In some embodiments, the input 280 is a touch-sensitive display, such as a touch-sensitive surface. In some embodiments, the user interface 278 includes one or more soft keyboard embodiments. The soft keyboard embodiments may include standard (QWERTY) and/or non-standard configurations of symbols on the displayed icons.

The regimen adjustment device 250 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the regimen adjustment device 250 and/or for determining an amount of physical exertion by the subject.

It should be appreciated that the regimen adjustment device 250 illustrated in FIG. 3 is only one example of a multifunction device that may be used for optimizing basal administration timing in a standing basal insulin regimen for a subject, and that the regimen adjustment device 250 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 192 of the regimen adjustment device 250 illustrated in FIG. 3 optionally includes high-speed random access memory and optionally also includes non-volatile memory, such as one or more magnetic disk storage devices, flash memory devices, or other non-volatile solid-state memory devices. Access to memory 192 by other components of the regimen adjustment device 250, such as CPU(s) 274 is, optionally, controlled by the memory controller 368.

In some embodiments, the memory 192 of the regimen adjustment device 250 illustrated in FIG. 3 optionally includes a third data set 302 comprising a plurality of insulin medicament records over the past time course. Each insulin medicament record 304 in the plurality of medicament records comprises: (i) a respective insulin medicament injection event 306 including an amount of insulin medicament injected 308 into the subject using a respective insulin pen 104 in the one or more insulin pens, (ii) a corresponding insulin event electronic timestamp 310 that is automatically generated by the respective insulin pen 104 upon occurrence of the respective insulin medicament injection event, and (iii) a respective type of insulin medicament 312 injected into the subject from one of (a) the basal insulin medicament and (b) the bolus insulin medicament.

In some embodiments, the memory 192 of the regimen adjustment device 250 illustrated in FIG. 3 optionally includes a meal record data set 314 comprising a plurality of meal records over the past time course. Each respective meal record 316 in the plurality of meal records comprises: (i) a carbohydrate intake event 318 (e.g., a meal such a breakfast, lunch, or dinner), and (ii) a corresponding carbohydrate timestamp 320 indicating when the respective carbohydrate intake event occurred.

In some embodiments, memory 192 of the regimen adjustment device 250 illustrated in FIG. 3 optionally includes a fourth data set 322 comprising the physical exertion of the subject over the past time course.

The peripherals interface 370 can be used to couple input and output peripherals of the device to CPU(s) 274 and memory 192. The one or more processors 274 run or execute various software programs and/or sets of instructions stored in memory 192, such as the basal timing adjustment module 204, to perform various functions for the regimen adjustment device 250 and to process data.

In some embodiments, the peripherals interface 370, CPU(s) 274, and memory controller 368 are, optionally, implemented on a single chip. In some other embodiments, they are implemented on separate chips.

RF (radio frequency) circuitry of network interface 284 receives and sends RF signals, also called electromagnetic signals. In some embodiments, the standing insulin regimen 206, the first data set 218, the fasting event data set 224, the second data set 228, the third data set 302, the meal record data set 314, and/or the fourth data set 310 is received using this RF circuitry from one or more devices such as a glucose sensor 102 associated with a subject, an insulin pen 104 associated with the subject and/or the data collection device 200. In some embodiments, the RF circuitry 108 converts electrical signals to/from electromagnetic signals and communicates with communications networks and other communications devices, glucose sensors 102, and insulin pens 104 and/or the data collection device 200 via the electromagnetic signals. The RF circuitry 284 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The RF circuitry 284 optionally communicates with the communication network 106. In some embodiments, the circuitry 284 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the adjustment timing device 250. The audio circuitry 372 receives audio data from the peripherals interface 370, converts the audio data to electrical signals, and transmits the electrical signals to the speaker 360. The speaker 360 converts the electrical signals to human-audible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 192 and/or the RF circuitry 284 by the peripherals interface 370.

In some embodiments, the power supply 276 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the regimen adjustment device 250 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the regimen adjustment device 250, opposite the display 282 on the front of the regimen adjustment device 250, so that the input 280 is enabled for use as a viewfinder for still and/or video image acquisition. In some embodiments, another optical sensor 373 is located on the front of the regimen adjustment device 250 so that the subject's image is obtained (e.g., to verify the health or condition of the subject, to determine the physical activity level of the subject, to help diagnose a subject's condition remotely, or to acquire visual physiological measurements 312 of the subject, etc.).

As illustrated in FIG. 3, a regimen adjustment device 250 preferably comprises an operating system 202 that includes procedures for handling various basic system services. The operating system 202 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the regimen adjustment device 250 is a smart phone. In other embodiments, the regimen adjustment device 250 is not a smart phone but rather is a tablet computer, desktop computer, emergency vehicle computer, or other form or wired or wireless networked device. In some embodiments, the regimen adjustment device 250 has any or all of the circuitry, hardware components, and software components found in the regimen adjustment device 250 depicted in FIG. 2 or 3. In the interest of brevity and clarity, only a few of the possible components of the regimen adjustment device 250 are shown in order to better emphasize the additional software modules that are installed on the adjustment timing device 250.

While the system 48 disclosed in FIG. 1 can work standalone, in some embodiments it can also be linked with electronic medical records to exchange information in any way.

Now that details of a system 48 for optimizing basal administration timing in a standing basal insulin regimen for a subject have been disclosed, details regarding a flow chart of processes and features of the system, in accordance with an embodiment of the present disclosure, are disclosed with reference to FIGS. 4A through 4E. In some embodiments, such processes and features of the system are carried out by the basal timing adjustment module 204 illustrated in FIGS. 2 and 3.

Block 402. With reference to block 402 of FIG. 4A, the goal of insulin therapy in subjects with either type 1 diabetes mellitus or type 2 diabetes mellitus is to match as closely as possible normal physiologic insulin secretion to control fasting and postprandial plasma glucose. As illustrated in FIG. 2, a regimen adjustment device 250 comprises one or more processors 274 and a memory 192/290. The memory stores instructions that, when executed by the one or more processors, perform a method for optimizing basal administration timing in a standing basal insulin regimen.

Blocks 404-406. Referring to block 404 of FIG. 4A, in the method, a standing basal insulin regimen 206 for the subject is obtained. The standing basal insulin regimen 206 for the subject comprises a total amount of basal insulin medicament 210 for a recurring period 208. An example of a recurring period 208 is one day and in such an example, the total amount of basal insulin medicament 210 is the amount of basal insulin medicament 210 the subject should take each day. The present disclosure is not limited to recurring periods that are one day and longer or shorter recurring periods are within the scope of the present disclosure.

The standing basal insulin regimen 206 further contains one or more basal injection event types in a set of basal injection event types for the recurring period. Referring to block 406 of FIG. 4A, examples of basal injection event types include "morning basal" which represents the portion of the total amount of basal insulin medicament 210 that is to be injected as a single injection event using an insulin pen 104 in the morning and "evening basal" which represents the portion of the total amount of basal insulin medicament 210 that is to be injected as a single injection event using an insulin pen 104 in the evening. The standing basal insulin regimen 206 further contains a respective apportionment 214 of the total amount of basal insulin medicament between each respective basal injection event type 212 in the one or more basal injection event types. For instance, in an example where the standing basal insulin regimen 206 consists of two the "morning basal" and "evening basal" injection event types, the respective apportionment 214 will indicate what percentage of the total amount of basal insulin medicament 210 is to be administered as the "morning basal" (e.g., forty percent, fifty percent, sixty percent) and what percentage of the total amount of basal insulin medicament 210 is to be administered as the "evening basal" (e.g., forty percent, fifty percent, sixty percent), where the respective apportionments collectively sum up to the entire total amount of the basal insulin medicament 210 for the recurring period. Thus, in the example where the standing basal insulin regimen 206 consists of two the "morning basal" and "evening basal" injection event types, the respective apportionment of the "morning basal" and "evening basal" sums up to 100 percent of the basal insulin medicament 210 for the recurring period.

In some embodiments, the basal insulin medicament specified by the basal insulin medicament dosage regimen 206 consists of a single insulin medicament having a duration of action that is between 12 and 24 hours or a mixture of insulin medicaments that collectively have a duration of action that is between 12 and 24 hours. Examples of such basal insulin medicaments include, but are not limited to, Insulin Degludec (developed by NOVO NORDISK under the brand name Tresiba), NPH (Schmid, 2007, "New options in insulin therapy," J Pediatria (Rio J). 83(Suppl 5): S146-S155), Glargine (LANTUS, Mar. 2, 2007), Insulin Glargine [rDNA origin] injection (Dunn et al. 2003, "An Updated Review of its Use in the Management of Diabetes Mellitus" Drugs 63: p. 1743), and Determir (Plank et al., 2005, "A double-blind, randomized, dose-response study investigating the pharmacodynamic and pharmacokinetic properties of the long-acting insulin analog detemir," Diabetes Care 28:1107-1112).

Blocks 408-410. Referring to block 408 of FIG. 4A, in the method, a first data set 216 is obtained. The past time course comprises a first plurality of instances of a recurring period. In some embodiments, the recurring period is one day and the past time course comprises a plurality of days (e.g., two days, three days, four days, or five or more days). The first data set 216 comprises a plurality of glucose measurements of the subject taken over the past time course. In typical embodiments, the glucose measurements are from one or more glucose sensors 102. FIG. 2 illustrates. Each such glucose measurement 218 is timestamped with a glucose measurement timestamp 220 to represent when the respective measurement was made. Thus, in some embodiments, the glucose measurements are measured without human intervention. That is, the subject does not manually make the glucose measurements. In alternative embodiments of the present disclosure, the subject or a health care practitioner manually takes glucose measurements and such manual glucose measurements are used as the glucose measurements 218 in the first data set 216.

In embodiments where autonomous glucose measurements are used in the first data set 216, devices such as the FREESTYLE LIBRE CGM by ABBOTT ("LIBRE") may serve as the glucose sensor 102 in order to make the plurality of autonomous glucose measurements of a subject. The LIBRE allows calibration-free glucose measurements with an on-skin coin-sized sensor, which can send up to eight hours of data to a reader device (e.g., the data collection device 200 and/or the regimen adjustment device 250) via near field communications, when brought close together. The LIBRE can be worn for fourteen days in all daily life activities. Referring to block 410 of FIG. 4A, in some embodiments, the glucose measurements 218 are autonomously taken from the subject at an interval rate of 5 minutes or less, 3 minutes or less, or 1 minute or less. In some embodiments, the glucose measurements 218 are taken from the subject at an interval rate of 5 minutes or less, 3 minutes or less, or 1 minute or less, over a time period of a day or more, two days or more, a week or more, or two weeks or more. In some embodiments, the glucose measurements 218 are autonomously taken (e.g., without human effort, without human intervention, etc.). In some embodiments the regimen adjustment device 250 further comprises a wireless receiver and the first data set 216 is obtained wirelessly from a glucose sensor 102 affixed to the subject (e.g., in accordance with an 802.11, Bluetooth, or ZigBee standard).

Figure 4C:
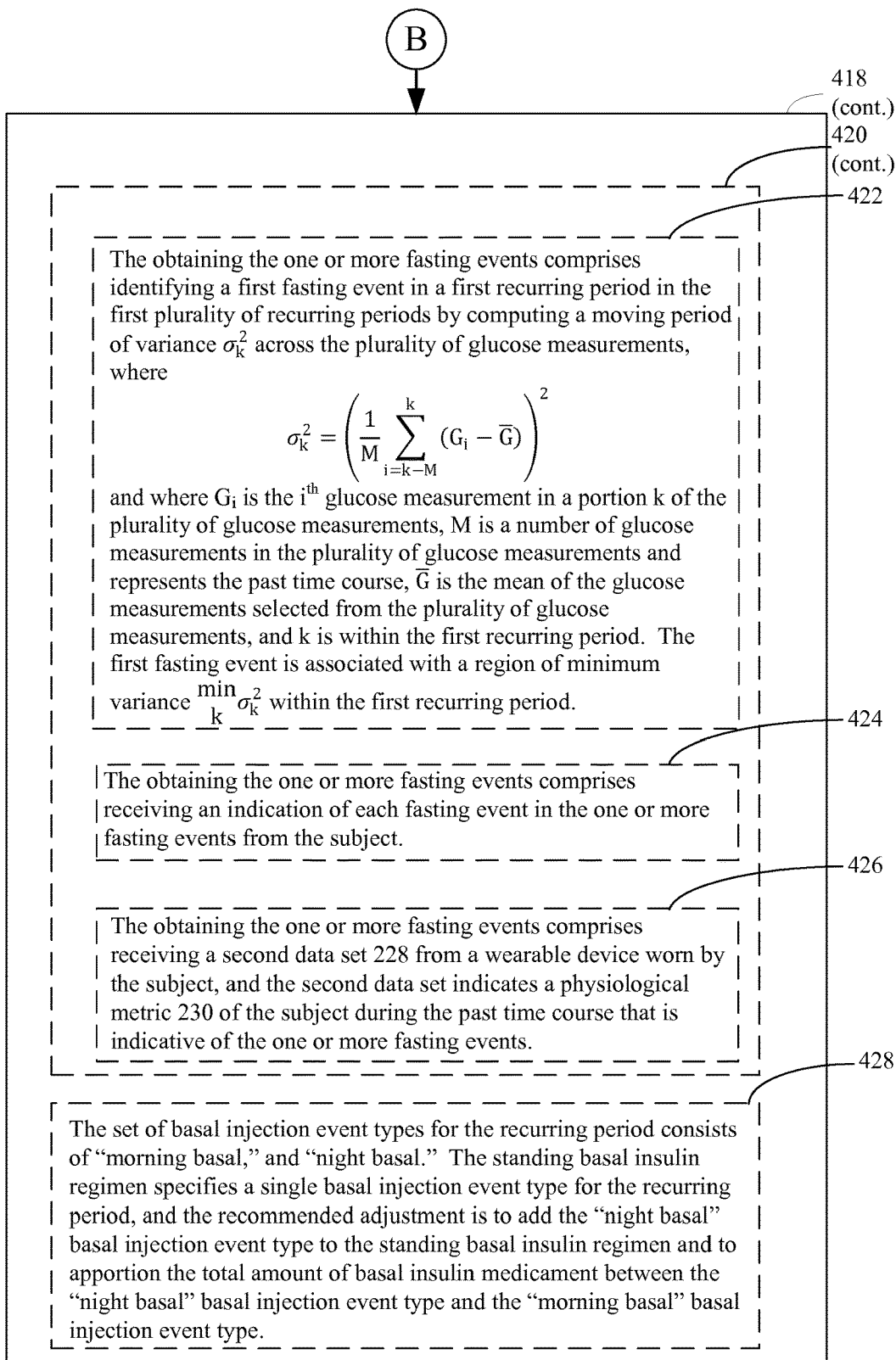

Referring to block 412 of FIG. 4A, in some embodiments, the past time course is the last week, the last two weeks, or the last month. Further, the method disclosed in FIGS. 4A through 4E is repeated on a recurring basis over time. Further still, the basal insulin medicament consists of a single insulin medicament having a duration of action that is between 12 and 24 hours or a mixture of insulin medicaments that collectively have a duration of action that is between 12 and 24 hours.

Figure 7:
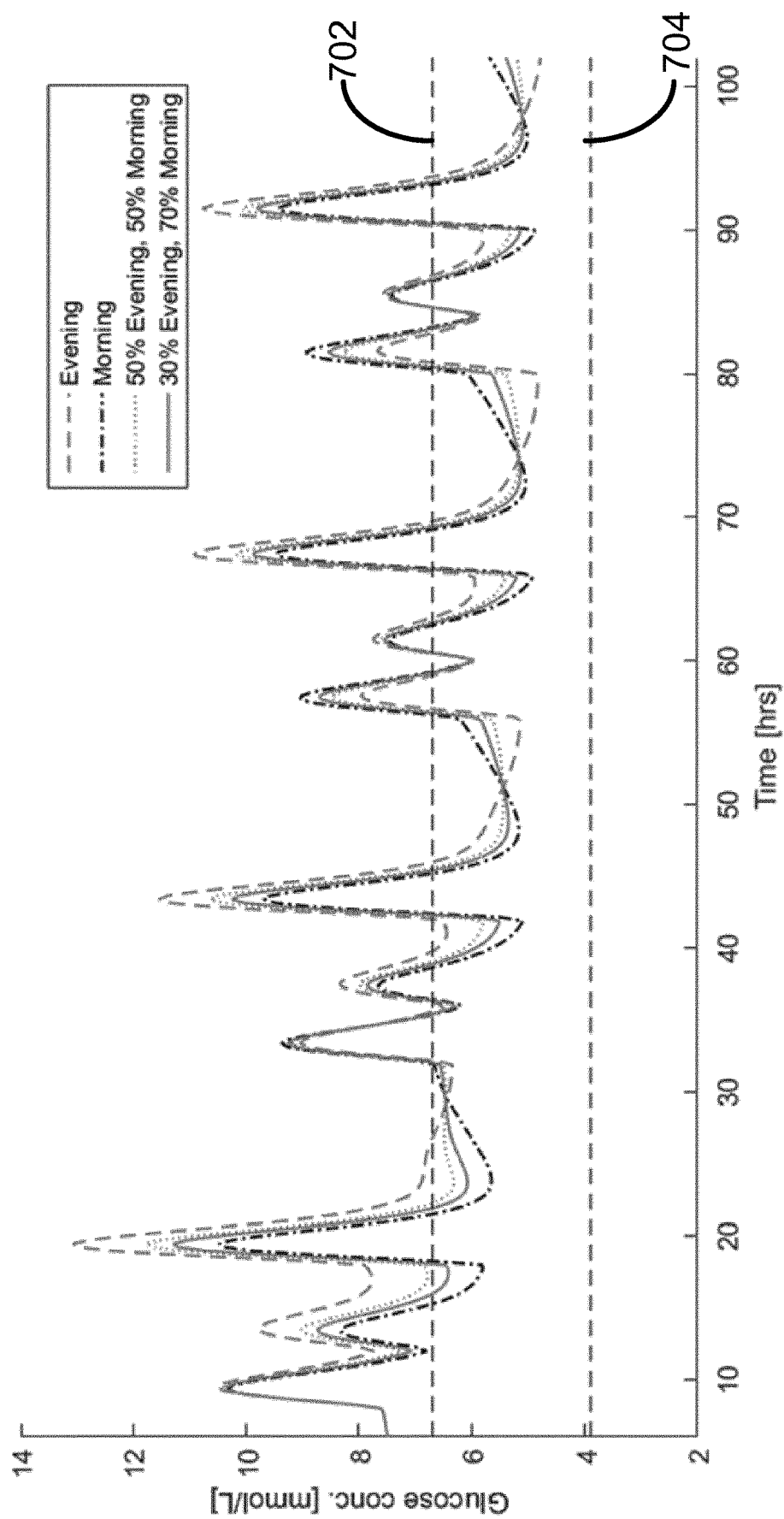
FIG. 7 illustrates how an optimization algorithm searches for a recommended adjustment comprising a change in a number of basal injection event types in a standing basal insulin regimen and/or a change in the respective apportionment of a total amount of basal insulin medicament between each respective basal injection event type in the one or more basal injection event types by simulating scenarios and measuring outcome in accordance with an embodiment of the present disclosure. The algorithm then suggests the recommended adjustment with the best outcome in accordance with an embodiment of the present disclosure.

Blocks 414-416. Referring to block 414 of FIG. 4B, the method continues with the evaluation of the plurality of glucose measurements of the first data set 216 over the past time course using a stop condition 222. The purpose of this evaluation is to ensure that the relative apportionment of the total amount of basal insulin medicament between the injection event types is optimal. FIG. 7 illustrates. In the example illustrated in FIG. 7 the glucose measurements of the first data set 218, as well as optionally insulin pen and meal data are used to identify parameters of a model describing insulin-glucose dynamics of the individual subject. The model with identified parameters allows for the simulation of different basal insulin medicament injection event apportionment scenarios, where different timings of basal injections are simulated and the results compared with respect to glycaemic outcome. This practice constitutes evaluation of the plurality of glucose measurements of the first data set 216 over the past time course using a stop condition 222. In some embodiments, included in this evaluation are basal split scenarios (e.g., where the basal injection event types used in the modeling is expanded to include more injection event types) and basal un-splitting scenarios (e.g., where the basal injection event types used in the modeling is compacted to include fewer injection event types). Further still, the apportionment of the total amount of basal insulin medicament across the different basal injection event types can also be determined using optimized using the modeling. In FIG. 7, four different apportionment scenarios are evaluated using a stop condition (1: 100 percent evening basal injection event; 2: 100 percent morning basal injection event; 3: 50 percent evening and 50 percent morning basal injection event; and 4: 30 percent evening and 70 morning basal injection event). Each of these apportionment scenarios is evaluated over a future time course for a stop condition. For instance, each of the apportionment scenarios are evaluated to determine if they better project a subject from glycaemic risks than the apportionment 214 found in the current standing insulin regimen 206. When this is the case, the stop condition is deemed satisfied and the apportionment of the total amount of basal insulin medicament 210 is reapportioned across the basal injection event types 212 in the standing insulin regimen 206 in accordance with the apportionment scenario that better protects the subject from glycaemic risks.

Referring to block 416 of FIG. 4B, in some embodiments, the first data set is filtered such that glucose measurements 218 from only those periods of time in which the subject is adhering to the standing insulin regimen are used. In such embodiments, glucose measurements taken during periods in which the subject is not in adherence with the standing insulin regimen 206 are not used. For instance, in some embodiments, a subject is deemed to not be adhering to the standing insulin regimen when the subject is taking the total amount of basal insulin medicament 210 but not according to the apportionment 214 specified by the standing insulin regimen 206. For example, if the standing insulin regimen 206 specifies a "morning basal" injection event type in which fifty percent of the total amount of basal insulin medicament 210 is to be injected with an insulin pen and an "evening basal" injection event type in which the other fifty percent of the total amount of basal insulin medicament 210 is to be injected, but the subject takes 80 percent of total amount of basal insulin medicament 210 in the morning on day, the subject is deemed to not be in adherence with the standing insulin regimen 206 for the day and all glucose measurements 218 taken that day are not used.

Thus, in accordance with block 416 of FIG. 4B, to determine standing regimen adherence, a third data set 302 is obtained from an insulin pen 104 used by the subject to apply the basal insulin regimen. The third data set comprises insulin medicament records. Each respective record 304 in the plurality of medicament records comprises: (i) an insulin medicament injection event 306 including an amount of basal insulin medicament injected 308 into the subject and (ii) a corresponding insulin event electronic timestamp 310 that is automatically generated by the insulin pen upon occurrence of the respective insulin medicament injection event. The third data set and the standing basal insulin regimen is then used to determine one or more recurring periods in the past time course that do not comply with the standing basal insulin regimen for the subject. Glucose measurements taken during these days are excluded from the stop condition evaluation.

Blocks 418 through 436. Blocks 418 through 436 of FIGS. 4B through 4E provide several different embodiments in accordance with the present disclosure for how the disclosed method proceeds to both evaluate the plurality of glucose measurements over the past time course using the stop condition 222 and what actions are taken when the stop condition is deemed to be satisfied. In particular, referring to block 418, when the stop condition is satisfied, a recommended adjustment is made that comprises a change in the number of basal injection event types in the standing basal insulin regimen and/or a change in the respective apportionment of the total amount of basal insulin medicament between each respective basal injection event type in the one or more basal injection event types.

An example of a recommended adjustment has been presented above in relation to FIG. 7. In FIG. 7, four different apportionment scenarios are evaluated using a stop condition (1: 100 percent evening basal injection event; 2: 100 percent morning basal injection event; 3: 50 percent evening and 50 percent morning basal injection event; and 4: 30 percent evening and 70 morning basal injection event). Each of these apportionment scenarios is evaluated over a future time course for a stop condition. For instance, each of the apportionment scenarios are evaluated to determine if they better project a subject from glycaemic risks than the apportionment 214 found in the current standing insulin regimen 206. When this is the case, the stop condition is deemed satisfied and the apportionment of the total amount of basal insulin medicament 210 is reapportioned across the basal injection event types 212 in the standing insulin regimen 206 in accordance with the apportionment scenario that better protects the subject from glycaemic risks.

Block 420 provides another such example of the determination of a recommended adjustment to the standing insulin regimen 206. In this embodiment, the standing basal insulin regimen 206 specifies a single basal injection event type 212 for the recurring period 208. In one example, one hundred percent of the total amount of basal insulin medicament 210 is to be administered with an insulin pen as a single "morning basal" injection event. In this embodiment, the evaluating the glucose measurements over the past time course using the stop condition 222 comprises obtaining fasting events in the past time course. Each fasting event 226 is associated with a different instance of the recurring period in the plurality of instances of the recurring period. For example, in the case where the recurring period is a day, each fasting event 226 is associated with a different day in the multi-day past time course. That is, if the recurring period is one day, an example of a "different instance" of the recurring period would be a particular day, such as Tuesday, May 5. For each respective fasting event 226 in the one or more fasting events, there is compared (i) one or more first glucose measurements (e.g., a single glucose measurement, a measure of central tendency of 2 or more glucose measurements) of the subject in the first data set occurring at a first time slot that is a first predetermined amount of time prior to (e.g., 2 hours before, 4 hours before, 6 hours before, 8 hours before, 10 hours before, 12 hours before, etc.) a beginning of the respective fasting event to (ii) one or more second glucose measurements (e.g., a single glucose measurement, a measure of central tendency of 2 or more glucose measurements) of the subject in the first data set occurring at a second time slot that is at a predetermined point within or after (e.g. 30 minutes after, one hour after, two hours after, three hours after, etc.) the respective fasting event, thereby obtaining one or more comparisons. Such comparisons are premised on the basis that if a subject takes one insulin dose per day and glucose measurements are high before bedtime but low before breakfast or vice versa, this indicates that the basal should be split.

Figure 6:
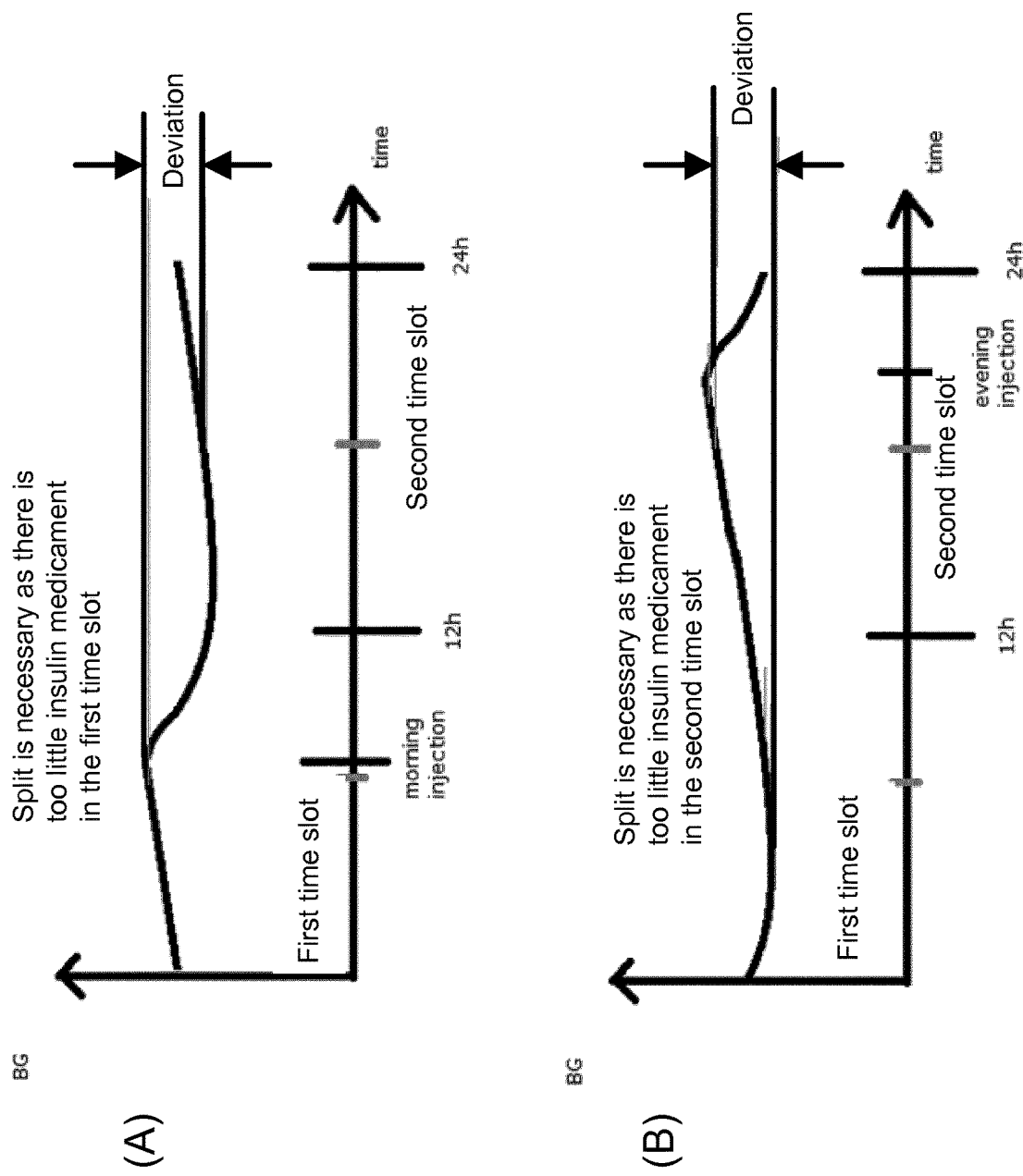
FIG. 6 illustrates instances where one or more glucose measurements from a second time slot trends higher than one or more glucose measurements from a first time slot (panel A) and where one or more glucose measurements from a second time slot trends lower than one or more glucose measurements from a first time slot (panel B) in accordance with an embodiment of the present disclosure.

FIG. 6 illustrates. Panel A of FIG. 6 illustrates the blood glucose concentration of a subject over a recurring period in which the contribution to glucose levels from meal events and associated short term insulin medicament (bolus) injection events have been subtracted out. Further in panel A, the subject takes 100 percent of the total amount of basal insulin medicament 210 as a morning basal bolus injection event 212. Comparison of the glucose measurements in the first time slot to the glucose measurements in the second time slot (which are obtained from the first data set 216 using the glucose measurement timestamps 220) shows a substantial deviation and indicates that there is insufficient insulin medicament during the first time slot. Panel B of FIG. 6 illustrates the blood glucose concentration of a different subject over a recurring period in which the contribution to glucose levels from meal events and associated bolus injection events has likewise been subtracted. Further in panel B, the subject takes 100 percent of the total amount of basal insulin medicament 210 as an evening basal bolus. Comparison of the glucose measurements in the first time slot to the glucose measurements in the second time slot for the subject of panel B shows a substantial deviation and indicates that there is insufficient insulin medicament during the second time slot. Thus, in both the situation of panel A and panel B of FIG. 6, the basal insulin medicament should be split into two injections events per recurring period.

Thus, as illustrated in FIG. 6, the stop condition in the embodiment of block 420 is satisfied when the comparisons indicate that the respective one or more first glucose measurements (of the first time slot) deviate from the corresponding respective one or more second glucose measurements (of the second time slot) by more than a threshold amount (e.g., by five percent or more, 10 percent or more, 15 percent or more, 20 percent or more, 25 percent or more, 30 percent or more, 35 percent or more, 40 percent or more, 45 percent or more, 50 percent or more, 55 percent or more, 60 percent or more, or 65 percent or more). In such embodiments, as discussed above for panels A and B of FIG. 6, the recommended adjustment is to increase the number of basal injection event types 212 to two (e.g., a "morning basal" and an "evening basal") and apportion the total amount of basal insulin medicament 210 between the two basal injection event types.

Embodiments such as that described in block 420 rely on the identification of fasting events during the past time course. Block 422 of FIG. 4C provides one way in accordance with the present disclosure in which such fasting events are identified. In accordance with block 422, a first fasting event 226 is identified in a first recurring period (e.g., a period of 24 hours) in the first plurality of recurring periods in the past time course represented by the first data set encompassed by the plurality of glucose measurements in the first data set 216 by first computing a moving period of variance $\sigma_k^2$ across the plurality of glucose measurements, where:

$$\sigma_k^2 = \left(\frac{1}{M}\sum_{i=k-M+1}^{k}(G_i - \overline{G})\right)^2$$

and where $G_i$ is the $i^{th}$ glucose measurement in a portion k of the plurality of glucose measurements, M is a number of glucose measurements in the plurality of glucose measurements and represents the past time course, $\overline{G}$ is the mean of the glucose measurements selected from the plurality of glucose measurements of the first data set 216, and k is within the first recurring time period. As an example, the glucose measurements may span several days or weeks, with glucose measurements taken every five minutes. A first time period k (e.g., one day) within this overall time span is selected and thus the portion k of the plurality of measurements is examined for a period of minimum variance. The first fasting period is deemed to be the period of minimum variance $$\min_k \sigma_k^2$$

within the first time period. Next, the process is repeated with portion k of the plurality of glucose measurements by examining the next portion k of the plurality of glucose measurements for another period of minimum variance thereby assigning another fasting period.

Moreover, in some embodiments, only those fasting events that are deemed standing insulin regimen 206 adherent are used. Example 1, below, illustrates a way in which a determination is made as to whether a fasting event 226 is standing insulin regimen 206 adherent. Moreover, European Patent Application Number EP16177080.5, entitled "Regimen Adherence Measure for Insulin Treatment Base on Glucose Measurement and Insulin Pen Data," filed Jun. 30, 2016, which is hereby incorporated by reference, discloses techniques for identifying and classifying fasting events as adherent or nonadherent. In some embodiments, only those fasting events that are classified as "basal regimen adherent" in accordance with European Patent Application Number EP16177080.5 are used to optimizing basal administration timing in a standing basal insulin regimen.

Block 424 of FIG. 4C provides another way in accordance with the present disclosure in which fasting events 224 are identified. In accordance with block 424, the obtaining of the one or more fasting events comprises receiving an indication of each fasting event in the one or more fasting events from the subject. In other words, in some embodiments, the identifying the one or more of fasting events comprises receiving an indication of each fasting event 226 in the one or more fasting events from the subject in the form of feed-forward events. Each respective feed-forward event represents an instance where the subject has indicated they are fasting or are about to fast. For instance, the user may indicate through a graphical user interface provided by the basal timing adjustment module 204 when the subject is fasting (e.g. has not eaten a meal in more than five hours, more than six hours, more than seven hours, more than eight hours, more than nine hours, or more than 10 hours, etc.).

Block 426 of FIG. 4C provides yet another way in accordance with the present disclosure in which fasting events 224 are identified. In accordance with block 426, the obtaining of the one or more fasting events comprises receiving a second data set 228 from a wearable device (e.g., from wearable physiological measurement devices, from measurement devices within the data collection device 200 such as a magnetometer or a thermostat, etc.) worn by the subject, and the second data set indicates a physiological metric 230 of the subject during the past time course that is indicative of the one or more fasting events. In some embodiments, the physiological metric measurement 230 is body temperature of the subject. In some embodiments, the physiological metric measurement 230 is a measurement of activity of the subject. In some embodiments, the optional accelerometer 317, optional GPS 319, and/or magnetometer (not shown) of the regimen adjustment device 250 or such components optionally within the one or more glucose monitors 102 and/or the one or more insulin pens 104 is used to acquire such physiological metric measurements 232. In some embodiments, both an autonomous fast detection algorithm, such as one disclosed in blocks 422 and/or 426, and the manual (user indicated) fast detection disclosed in block 424 are used for detecting fasting events. For instance, in some embodiments, a fasting event 226 that has been autonomously detected (e.g., using the algorithm of block 422) is then verified using the feed-forward events of block 424 and/or 426. To illustrate, when a fasting event 226 autonomously detected using an algorithm such as one disclosed in block 422 is matched in time (temporally matched) to a feed-forward event in which the subject indicated they are fasting and/or a physiological metric 230 that indicated they are fasting, the fasting event 226 is deemed verified and used in further steps of the present disclosure. In some embodiments, a fasting event 226 must be verified in this manner and also be deemed insulin regimen 206 adherent (e.g., deemed standing insulin regimen 206 adherent as disclosed in Example 1 below).

Referring to block 428 of FIG. 4C, in some embodiments, the set of possible basal injection event types 212 for the recurring period specified by the standing insulin regimen 206 consists of "morning basal," and "night basal." In some such embodiments, the standing insulin regimen 206 specifies a single basal injection event type for the recurring period, the "morning basal" injection event type, and the recommended adjustment of block 418 is to add the "night basal" basal injection event type to the standing insulin regimen (e.g., in response to the scenario of FIG. 6, panel A) and to apportion the total amount of basal insulin medicament 210 between the "night basal" basal injection event type and the "morning basal" basal injection event type.

Figure 4D:
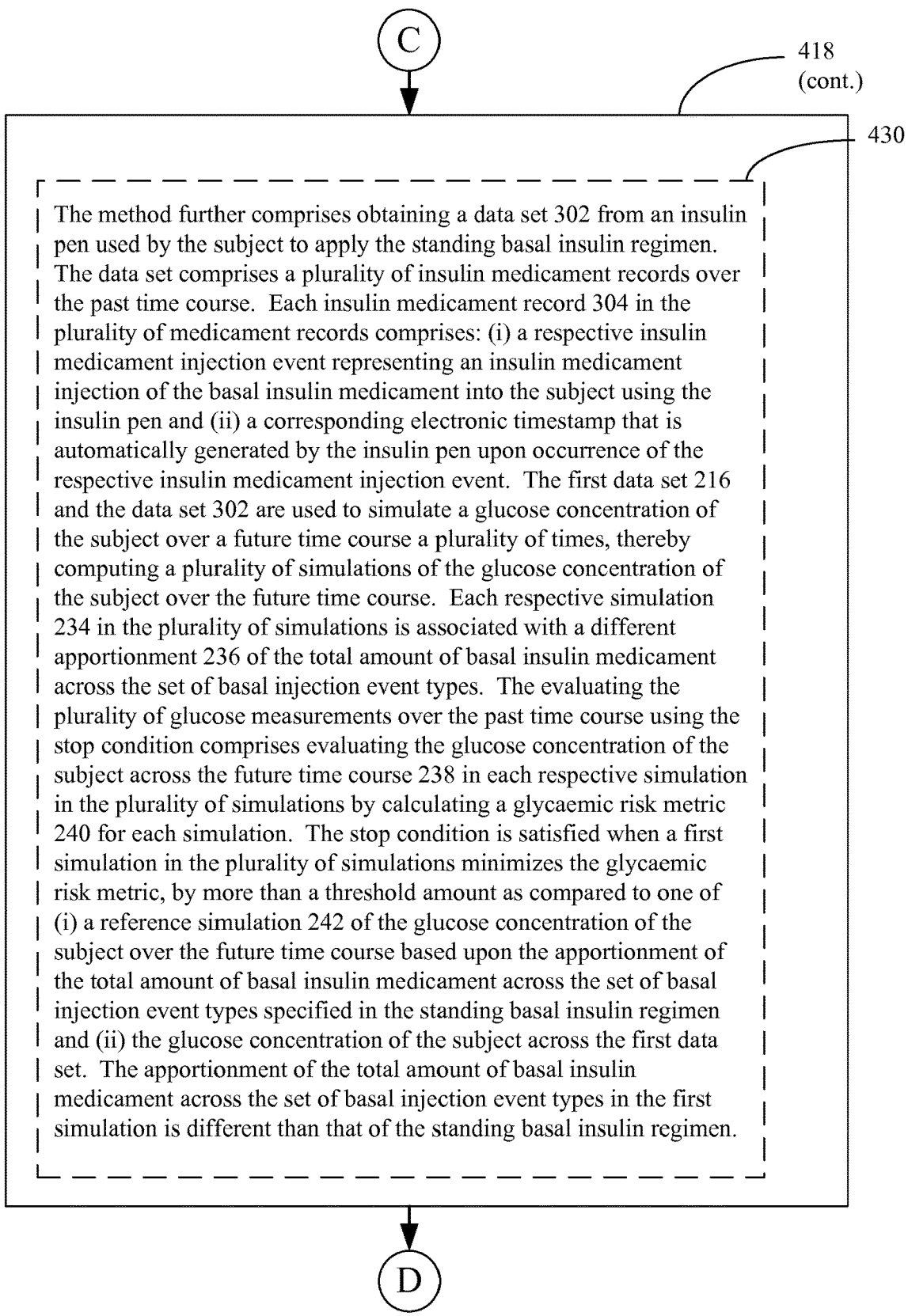

Referring to block 430 of FIG. 4D, in some embodiments the method further comprises obtaining a data set 302 from an insulin pen used by the subject to apply the standing basal insulin regimen. The data set 302 comprises a plurality of insulin medicament records over the past time course. Each insulin medicament record 304 in the plurality of medicament records comprises: (i) a respective insulin medicament injection event 306 representing an insulin medicament injection of the basal insulin medicament into the subject using the insulin pen and (ii) a corresponding insulin event electronic timestamp 310 that is automatically generated by the insulin pen upon occurrence of the respective insulin medicament injection event. The first data set 216 and the data set 302 are used to simulate a glucose concentration of the subject over a future time course a plurality of times, thereby computing a plurality of simulations of the glucose concentration of the subject over the future time course. FIG. 7 illustrates such simulations. As illustrated in FIG. 7, each respective glucose concentration simulation 234 in the plurality of simulations is associated with a different apportionment 236 of the total amount of basal insulin medicament across the set of basal injection event types. For instance:

100% taken in the morning
100% taken at night
80%/20% morning/night
70%/30% morning/night
60%/40% morning/night
50%/50% morning/night
40%/60% morning/night
30%/70% morning/night
20%/80% morning/night In such embodiments, the evaluating the plurality of glucose measurements over the past time course using the stop condition comprises evaluating the glucose concentration of the subject across the future time course 238 in each respective simulation in the plurality of simulations by calculating a glycaemic risk metric 240 (e.g., blood glucose variance, time in a desired glucose target range, estimated HbA1c) for each simulation. That is, the glucose measurements 218 of the first data set, and optionally the insulin pen data of the third data set 302, and optionally the meal data of the meal record data set (FIG. 3) are used to identify parameters of a model (e.g., insulin sensitivity factor) describing insulin-glucose dynamics of the individual subject. The model with identified parameters allows for the simulation of apportionment scenarios of the total amount of basal insulin medicament 210 across the set of basal injection event types, where different timings of basal injections are simulated and the results compared with respect to glycaemic outcome. The stop condition is satisfied when a first simulation in the plurality of simulations minimizes the glycaemic risk metric, by more than a threshold amount as compared to one of (i) a reference simulation 242 of the glucose concentration of the subject over the future time course based upon the apportionment of the total amount of basal insulin medicament across the set of basal injection event types specified in the standing basal insulin regimen 206 and (ii) the glucose concentration of the subject across the first data set. This threshold amount is application specific, dependent upon the parameters of the model describing insulin-glucose dynamics of the individual subject, as well as the glycaemic risk metric.

Thus, consider the case in which the standing insulin regimen 206 specifies that 100% apportionment of the total amount of basal insulin medicament 210 is to be taken as a single basal injection event 212 in the morning in each recurring period. A reference simulation 242 of the glucose concentration of the subject over the future time course using the insulin-glucose dynamics of the individual subject may be taken with this 100% apportionment and the glycaemic risk metric for this reference simulation evaluated. Also a simulation 242 of the glucose concentration of the subject over the future time course using the same insulin-glucose dynamics of the individual subject but with 50%/50% morning/night apportionment of the total amount of basal insulin medicament 210 each recurring period and the glycaemic risk metric for this simulation evaluated. If the 50%/50% morning/night apportionment produces a better value for the glycaemic risk metric than the 100% apportionment of the total amount of basal insulin medicament 210 to morning, than the stop condition is satisfied and the recommended adjustment comprises changing the apportionment of the total amount of basal insulin medicament 210 from 100% morning apportionment per recurring period to a 50%/50% morning/night apportionment per recurring period.

Alternatively, again consider the case in which the standing insulin regimen 206 specifies that 100% apportionment of the total amount of basal insulin medicament 210 is to be taken as a single basal injection event 212 in the morning in each recurring period. A reference simulation 242 of the glucose concentration of the subject over the future time course using the insulin-glucose dynamics of the individual subject is not taken with this 100% apportionment. Rather the glucose measurements from the past time course during which the 100% apportionment was imposed in the standing insulin regimen 206 are used to compute the glycaemic risk metric. Also a simulation 242 of the glucose concentration of the subject over the future time course using the insulin-glucose dynamics derived for the individual subject from the data acquired during the past time course (e.g., the glucose measurements 218, etc.) but with 50%/50% morning/night apportionment of the total amount of basal insulin medicament 210 each recurring period and the glycaemic risk metric for this simulation is evaluated. If the 50%/50% morning/night apportionment produces a better value for the glycaemic risk metric than the glycaemic risk metric computed using the glucose measurements from the first data set 216, than the stop condition is satisfied and the recommended adjustment comprises changing the apportionment of the total amount of basal insulin medicament 210 from 100% morning apportionment per recurring period to a 50%/50% morning/night apportionment per recurring period.

Referring to block 432 of FIG. 4E, and using FIG. 7 to illustrate examples of first and second threshold values, in some embodiments the glycaemic risk metric comprises (i) a total glucose level variability observed across the respective simulation, (ii) a variability in a plurality of fasting glucose levels calculated across the respective simulation, (iii) a percentage of time that a total glucose level exceeds a first threshold value 702 or falls below a second threshold 704 value across the respective simulation, or (iv) a percentage of time that an HbA1c level exceeds a third threshold value or falls below a fourth threshold value across the respective simulation. In instances where a glycaemic risk metric computed for a simulation is compared to a glycaemic risk metric computed using the glucose measurements in the first data set, the glycaemic risk metric for the first data set is computed using the glucose measurements levels within the first data set.

Figure 4E:
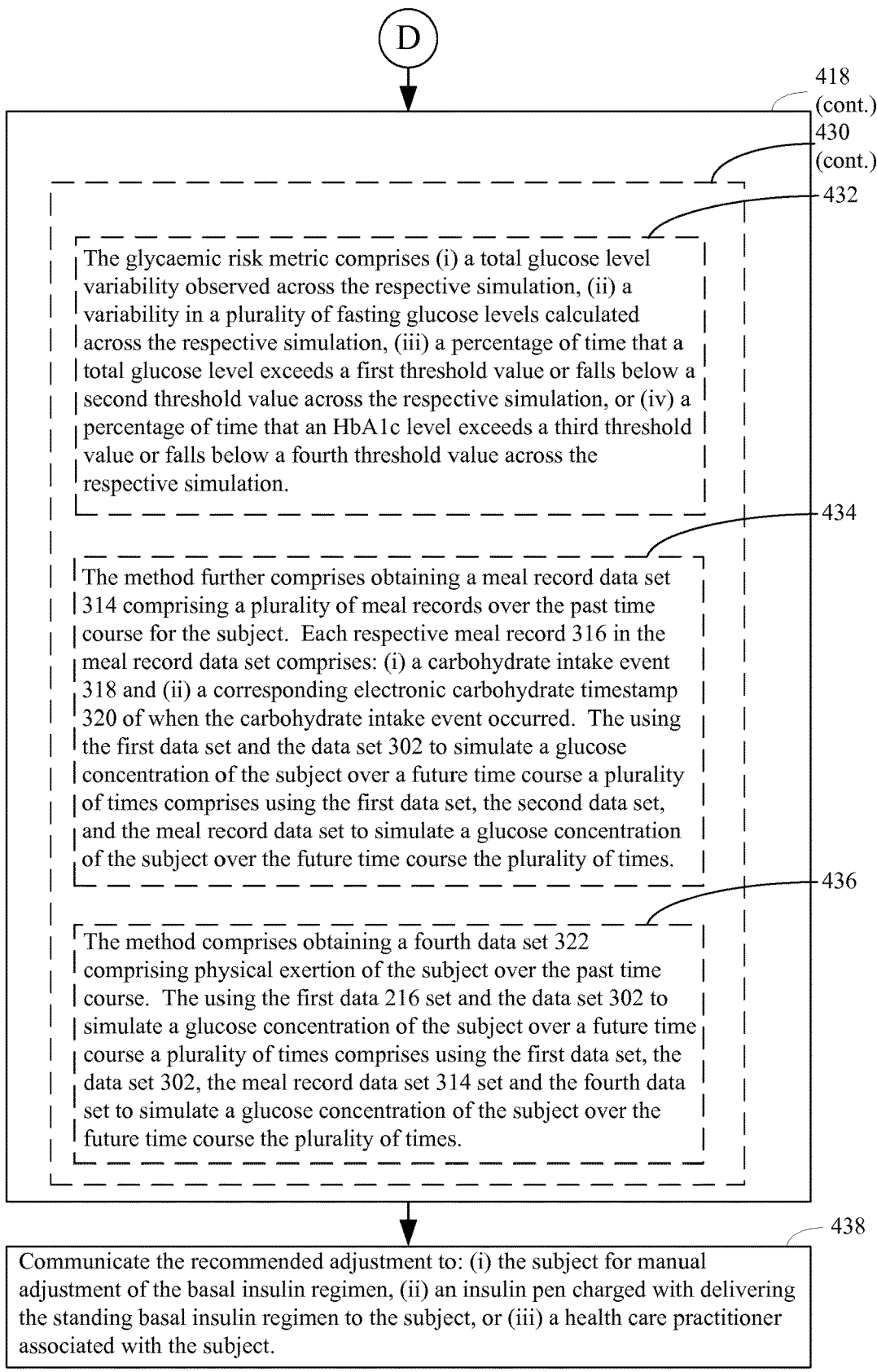

Referring to block 434 of FIG. 4E, and as discussed above, in some embodiments, the method further comprises obtaining a meal record data set 314 comprising a plurality of meal records over the past time course for the subject. Each respective meal record 316 in the meal record data set comprises: (i) a carbohydrate intake event 318 and (ii) a corresponding electronic carbohydrate timestamp 320 of when the carbohydrate intake event occurred. In such embodiments, the using the first data set and the second data set are used to simulate a glucose concentration of the subject over a future time course a plurality of times comprises using the first data set, the second data set, and the meal record data set to simulate a glucose concentration of the subject over the future time course the plurality of times. That is, the glucose measurements of the first data set 218, as well as insulin pen data and meal data are used to identify parameters of a model describing insulin-glucose dynamics of the individual subject. The model with identified parameters is then used to simulated different basal insulin medicament injection event apportionment scenarios, where the different timings of basal injections are simulated and the glycaemic risk metric is calculated for each simulation.

Referring to block 436 of FIG. 4E, in some embodiments, a fourth data set 322 comprising physical exertion of the subject over the past time course is obtained. In such embodiments, the using the first data set 216 and the data set 302 to simulate a glucose concentration of the subject over a future time course a plurality of times comprises using the first data set 216, the data set 302, the meal record data set 314 and the fourth data set 322 to simulate a glucose concentration of the subject over the future time course the plurality of times. That is, the glucose measurements of the first data set 218, as well as insulin pen data, meal data and physical exertion data are used to identify parameters of a model describing insulin-glucose dynamics of the individual subject. The model with identified parameters is then used to simulated different basal insulin medicament injection event apportionment scenarios, where the different timings of basal injections are simulated and the glycaemic risk metric is calculated for each simulation.

Figure 8:
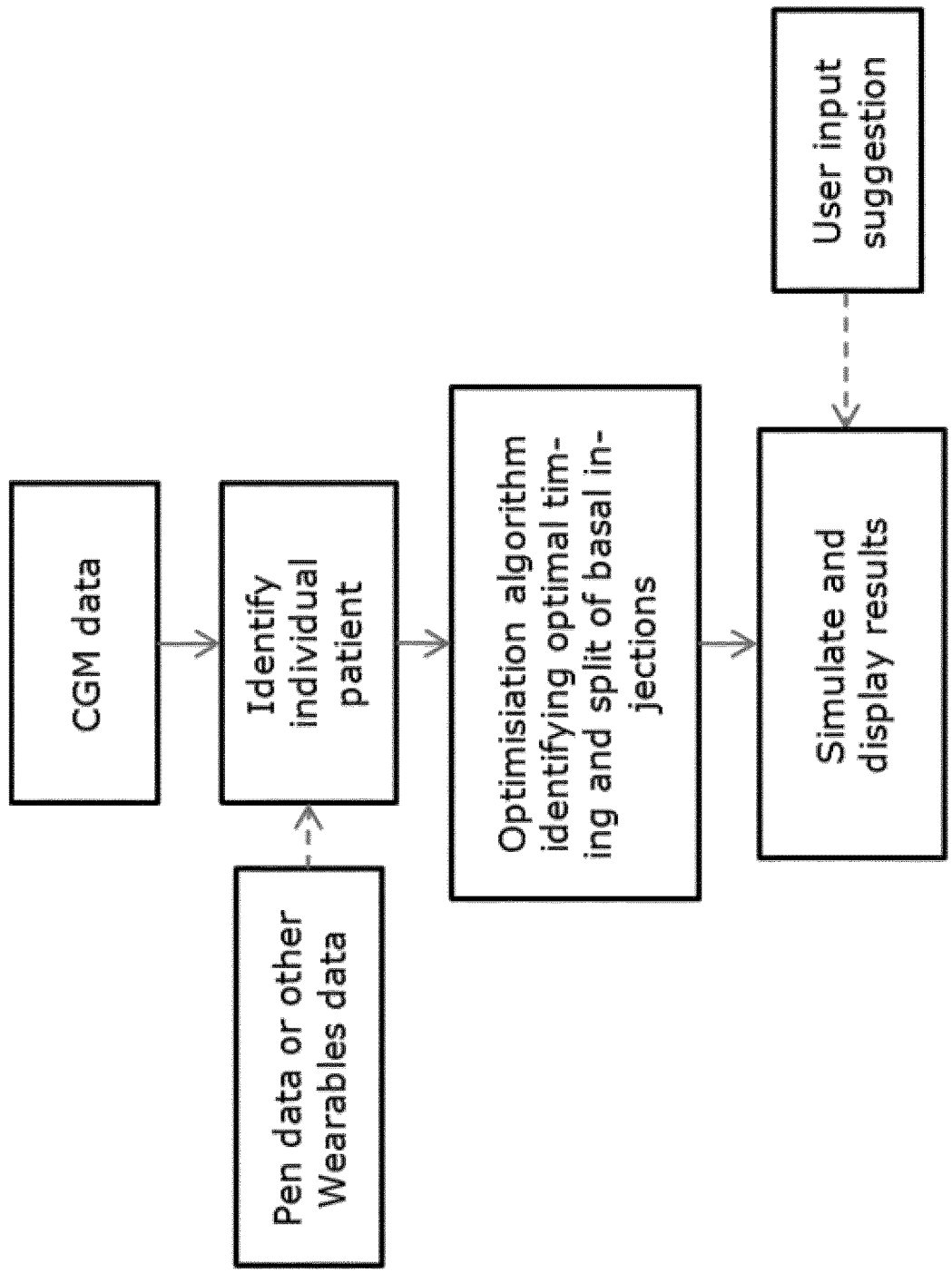
FIG. 8 illustrates an exemplary algorithm for optimizing basal administration timing in a standing basal insulin regimen for a subject in accordance with an embodiment of the present disclosure.

Block 438. Referring to block 438 of FIG. 4E, the method continues by communicating the recommended adjustment to the standing basal insulin regimen, when the determination is made to make the recommended adjustment to the standing basal insulin regimen for the subject, to: (i) the subject for manual adjustment of the standing basal insulin regimen, (ii) each insulin pen 104 in one or more insulin pens charged with delivering the standing basal insulin regimen to the subject, as dosage adjustment instructions, or (iii) a health care practitioner associated with the subject. FIG. 8 illustrates an exemplary embodiment of the method disclosed in FIGS. 4A through 4E.

Example 1: Use of glucose measurements to determine whether a fasting event is insulin regimen adherent. In some embodiments, the first data set 216 comprising a plurality of glucose measurements is obtained. In some embodiments the glucose measurements are obtained autonomously, for instance by a continuous glucose monitor 102. In this example, in addition to the autonomous glucose measurements, insulin administration events are obtained in the form of insulin medicament injection events 306 from one or more insulin pens 104 used by the subject to apply the standing insulin regimen 206. These insulin medicament records 304 may be in any format, and in fact may be spread across multiple files or data structures. As such, in some embodiments, the instant disclosure leverages the recent advances of insulin administration pens, which have become "smart" in the sense that they can remember the timing and the amount of insulin medicament administered in the past. One example of such an insulin pen 104 is the NovoPen 5. Such pens assists patients in logging doses and prevent double dosing. It is contemplated that insulin pens will be able to send and receive insulin medicament dose volume and timing, thus allowing the integration of continuous glucose monitors 102, insulin pens 104 and the algorithms of the present disclosure. As such, insulin medicament records 304 from one or more insulin pens 104 is contemplated, including the wireless acquisition of such data from the one or more insulin pens 104.

In some embodiments, each insulin medicament record 304 comprises: (i) a respective insulin medicament injection event 306 including an amount of insulin medicament injected 308 into the subject using a respective insulin pen 104 in the one or more insulin pens and (ii) a corresponding insulin event electronic timestamp 310 that is automatically generated by the respective insulin pen 104 upon occurrence of the respective insulin medicament injection event 306.

In some embodiments, a fasting event 226 is identified using the glucose measurements 218 of the subject and their associated glucose measurement timestamps 220 in the first data set 216. Once a fasting event is identified, e.g., by a method described in any one of blocks 422-426 above, or any other method, a classification is applied to the fasting event 224. The classification is one of "insulin regimen adherent" and "insulin regimen nonadherent."

A fasting event 226 is deemed insulin regimen adherent when the acquired one or more medicament records 304 establish, on a temporal and quantitative basis, adherence with the standing insulin medicament regimen 206 during the fasting event 226. A fasting event 226 is deemed insulin regimen nonadherent when the acquired one or more medicament records 304 do not include one or more medicament records that establish, on a temporal and quantitative basis, adherence with the standing insulin regimen 206 during the fasting event 226. In some embodiments, the standing insulin medicament regimen 206 specifies that a dosage of the basal insulin medicament is to be taken during each respective recurring period (e.g., day, twelve hour period) in a plurality of recurring periods and that a fasting event 226 is deemed insulin regimen nonadherent when there are no insulin medicament records 304 for the recurring period associated with the fasting event 226. In various embodiments, each recurring period in the plurality of recurring periods is two days or less, one day or less, or 12 hours or less. Thus, consider the case where the first data set 216 is used to identify a fasting event 226 and the standing insulin regimen 206 specifies to take dosage A of a basal insulin medicament every 24 hours. In this example, therefore, the recurring period is one day (24 hours). The fasting event 226 is inherently timestamped because it is derived from a period of minimum variance in timestamped glucose measurements, or by other forms of analysis of the timestamped glucose measurements 218 or by other means as disclosed in blocks 424 and 426 of FIG. 4C. Thus, the glucose measurement timestamp, or period of fasting (fasting event time period 228), represented by a respective fasting event 226 is used as a starting point for examining whether the fasting event is insulin regimen adherent. For instance, if the period of fasting associated with the respective timestamp includes 6:00 AM on Tuesday, May 17, what is sought in the insulin medicament records 304 is evidence that the subject took dosage A of the basal insulin medicament in the 24 hour period (the recurring period) leading up to 6:00 AM on Tuesday, May 17 (and not more or less of the prescribed dosage). If the subject took the prescribed dosage of the basal insulin medicament during this recurring period, and in accordance with the respective apportionments 214 across the basal injection event types 212 for the recurring period, the fasting event is deemed insulin regimen adherent. If the subject did not take the dose of the basal insulin medicament during this recurring period (or took more than the dose of the basal insulin medicament during this period specified by the standing insulin regimen 206, or did not adhere to the respective apportionments 214 across the basal injection event types 212 for the recurring period, the fasting event 224 is deemed to be insulin regimen nonadherent.

LIST OF EMBODIMENTS

1. A device (250) for optimizing basal administration timing in a standing basal insulin regimen (206) for a subject, wherein the device comprises one or more processors (274)

and a memory (192/290), the memory storing instructions that, when executed by the one or more processors, perform a method of:

obtaining the standing basal insulin regimen for the subject, wherein the standing basal insulin regimen specifies (i) a total amount of basal insulin medicament (210) for a recurring period (208), (ii) one or more basal injection event types in a set of basal injection event types for the recurring period, and (iii) a respective apportionment (214) of the total amount of basal insulin medicament between each respective basal injection event type (212) in the one or more basal injection event types;

obtaining a first data set (216), the first data set comprising a plurality of glucose measurements of the subject over a past time course, the past time course comprising a first plurality of instances of the recurring period and, for each respective glucose measurement (218) in the plurality of glucose measurements, a glucose measurement timestamp (220) representing when the respective measurement was made;

evaluating the plurality of glucose measurements over the past time course using a stop condition (222), wherein, when the stop condition is satisfied, the method further comprises:

determining a recommended adjustment comprising a change in the number of basal injection event types in the standing basal insulin regimen and/or a change in the respective apportionment of the total amount of basal insulin medicament between each respective basal injection event type in the one or more basal injection event types; and communicating the recommended adjustment to: (i) the subject for manual adjustment of the standing basal insulin regimen, (ii) an insulin pen charged with delivering the standing basal insulin regimen to the subject, or (iii) a health care practitioner associated with the subject.

2. The device of embodiment 1, wherein
the standing basal insulin regimen specifies a single basal injection event type for the recurring period, and
the evaluating the plurality of glucose measurements over the past time course using the stop condition comprises:
obtaining one or more fasting events in the past time course, wherein each fasting event (226) is associated with a different instance of the recurring period in the first plurality of instances of the recurring period,
comparing, for each respective fasting event in the one or more fasting events, (i) one or more first glucose measurements of the subject in the first data set occurring at a first time slot that is a first predetermined amount of time prior to a beginning of the respective fasting event to (ii) one or more second glucose measurements of the subject in the first data set occurring at a second time slot that is at a predetermined point within or after the respective fasting event, thereby obtaining one or more comparisons, wherein,
the stop condition is satisfied when the one or more comparisons indicate that the respective one or more first glucose measurements deviate from the corresponding respective one or more second glucose measurements by more than a threshold amount, and
the recommended adjustment is to increase the number of basal injection event types to two basal injection event types and to apportion the total amount of basal insulin medicament between the two basal injection event types.

3. The device of embodiment 1, wherein
the standing basal insulin regimen specifies a single basal injection event type for the recurring period, and
the evaluating the plurality of glucose measurements over the past time course using the stop condition comprises:
obtaining a plurality of fasting events in the past time course, wherein each fasting event (226) is associated with a different instance of the recurring period in the first plurality of instances of the recurring period,
obtaining, for each respective fasting event in the plurality of fasting events, (i) a first glucose measurements of the subject in the first data set occurring at a first time slot that is a first predetermined amount of time prior to a beginning of the respective fasting, and (ii) a second glucose measurements of the subject in the first data set occurring at a second time slot that is at a predetermined point within or after the respective fasting event,
obtaining a first measure of central tendency of the first glucose measurement of each fasting event in the plurality of fasting event, and a second measure of central tendency of the second glucose measurement of each fasting in the plurality of fasting events, and
comparing the first measure of central tendency to the second measure of central tendency, and thereby obtaining a comparison, wherein, the stop condition is satisfied when the comparison indicate that the respective first measure of central tendency deviate from the second measure of central tendency by more than a threshold amount, and
the recommended adjustment is to increase the number of basal injection event types to two basal injection event types and to apportion the total amount of basal insulin medicament between the two basal injection event types.

4. The device of embodiment 2 or 3, wherein the obtaining the one or more fasting events comprises identifying a first fasting event in a first recurring period in the first plurality of recurring periods by computing a moving period of variance $\sigma_k^2$ across the plurality of glucose measurements, wherein:

$$\sigma_k^2 = \left( \frac{1}{M} \sum_{i=k-M+1}^{k} (G_i - \bar{G}) \right)^2$$

wherein,
$G_i$ is the $i^{th}$ glucose measurement in a portion k of the plurality of glucose measurements,
M is a number of glucose measurements in the plurality of glucose measurements and represents the past time course,
$\bar{G}$ is the mean of the glucose measurements selected from the plurality of glucose measurements, and
k is within the first recurring period; and
associating the first fasting event with a region of minimum variance $$\min_{k} \sigma_k^2$$

within the first recurring period.

5. The device of embodiment 2 or 3, wherein the obtaining the one or more fasting events comprises receiving an indication of each fasting event in the one or more fasting events from the subject.

6. The device of embodiment 2 or 3, wherein
the obtaining the one or more fasting events comprises receiving a second data set (228) from a wearable device worn by the subject, and
the second data set indicates a physiological metric (230) of the subject during the past time course that is indicative of the one or more fasting events.

7. The device of any one of embodiments 1-6, the method further comprising:
obtaining a third data set (302) from an insulin pen (104) used by the subject to apply the standing basal insulin regimen, the third data set comprising a plurality of insulin medicament records, each respective insulin medicament record (304) in the plurality of medicament records comprising: (i) a respective insulin medicament injection event (306) including an amount of basal insulin medicament injected (308) into the subject and (ii) a corresponding insulin event electronic timestamp (310) that is automatically generated by the insulin pen upon occurrence of the respective insulin medicament injection event, and
using the third data set and the standing basal insulin regimen to determine one or more recurring periods in the past time course that do not comply with the standing basal insulin regimen for the subject; and
excluding from the stop condition evaluation those glucose measurements in the one or more recurring periods in the past time course that do not comply with the standing basal insulin regimen.

8. The device of embodiment 1, wherein
the set of basal injection event types for the recurring period consists of "morning basal," and "night basal,"
the standing basal insulin regimen specifies a single basal injection event type for the recurring period of "morning basal," and
the recommended adjustment is to add the "night basal" basal injection event type to the standing basal insulin regimen and to apportion the total amount of basal insulin medicament between the "night basal" basal injection event type and the "morning basal" basal injection event type.

9. The device of embodiment 1, wherein the method further comprises:
obtaining a second data set from an insulin pen used by the subject to apply the standing basal insulin regimen, the second data set comprising a plurality of insulin medicament records over the past time course, each insulin medicament record in the plurality of medicament records comprising: (i) a respective insulin medicament injection event representing an insulin medicament injection of the basal insulin medicament into the subject using the insulin pen and (ii) a corresponding electronic timestamp that is automatically generated by the insulin pen upon occurrence of the respective insulin medicament injection event; and
using the first data set and the second data set to simulate a glucose concentration of the subject over a future time course a plurality of times, thereby computing a plurality of simulations of the glucose concentration of the subject over the future time course, wherein each respective simulation (234) in the plurality of simulations is associated with a different apportionment (236) of the total amount of basal insulin medicament across the set of basal injection event types,
the evaluating the plurality of glucose measurements over the past time course using the stop condition comprises evaluating the glucose concentration of the subject across the future time course (238) in each respective simulation in the plurality of simulations by calculating a glycaemic risk metric (240) for each simulation,
the stop condition is satisfied when a first simulation in the plurality of simulations minimizes the glycaemic risk metric, by more than a threshold amount as compared to one of (i) a reference simulation (242) of the glucose concentration of the subject over the future time course based upon the apportionment of the total amount of basal insulin medicament across the set of basal injection event types specified in the standing basal insulin regimen and (ii) the glucose concentration of the subject across the first data set, and
the apportionment of the total amount of basal insulin medicament across the set of basal injection event types in the first simulation is different than that of the standing basal insulin regimen.

10. The device of embodiment 9, wherein the glycaemic risk metric comprises:
(i) a total glucose level variability observed across the respective simulation,
(ii) a variability in a plurality of fasting glucose levels calculated across the respective simulation,
(iii) a percentage of time that a total glucose level exceeds a first threshold value or falls below a second threshold value across the respective simulation, or
(iv) a percentage of time that an HbA1c level exceeds a third threshold value or falls below a fourth threshold value across the respective simulation.

11. The device of embodiment 9 or 10, the method further comprising:
obtaining a meal record data set (314) comprising a plurality of meal records over the past time course for the subject, each respective meal record (316) in the meal record data set comprising: (i) a carbohydrate intake event (318) and (ii) a corresponding electronic carbohydrate timestamp (320) of when the carbohydrate intake event occurred; and wherein
the using the first data set and the second data set to simulate a glucose concentration of the subject over a future time course a plurality of times comprises using the first data set, the second data set, and the meal record data set to simulate a glucose concentration of the subject over the future time course the plurality of times.

12. The device of embodiment 11, the method further comprising:
obtaining a fourth data set (322) comprising physical exertion of the subject over the past time course and wherein
the using the first data set and the second data set to simulate a glucose concentration of the subject over a future time course a plurality of times comprises using the first data set, the second data set, the third data set and the fourth data set to simulate a glucose concentration of the subject over the future time course the plurality of times.

13. The device of embodiment 1, wherein
the set of basal injection event types for the recurring period consists of "morning basal" and "night basal," and
the recurring period is a day.
14. The device of any one of embodiments 1-13, wherein successive measurements in the plurality of glucose measurements in the first data set are autonomously taken from the subject at an interval rate of 5 minutes or less, 3 minutes or less, or 1 minute or less.
15. The device of embodiment 1, wherein
the past time course is the last week, the last two weeks, or the last month and wherein the method is repeated on a recurring basis over time, and
the basal insulin medicament consists of a single insulin medicament having a duration of action that is between 12 and 24 hours or a mixture of insulin medicaments that collectively have a duration of action that is between 12 and 24 hours.
16. A method for optimizing basal administration timing in a standing basal insulin regimen for a subject, the method comprising:
obtaining the standing basal insulin regimen for the subject, wherein the standing basal insulin regimen specifies (i) a total amount of basal insulin medicament for a recurring period, (ii) one or more basal injection event types in a set of basal injection event types for the recurring period, and (iii) a respective apportionment of the total amount of basal insulin medicament between each respective basal injection event type in the one or more basal injection event types;
obtaining a first data set, the first data set comprising a plurality of glucose measurements of the subject over a past time course, the past time course comprising a first plurality of instances of the recurring period and, for each respective glucose measurement in the plurality of glucose measurements, a timestamp representing when the respective measurement was made;
evaluating the plurality of glucose measurements over the past time course using a stop condition, wherein, when the stop condition is satisfied, the method further comprises:
determining a recommended adjustment comprising a change in the number of basal injection event types in the standing basal insulin regimen and/or a change in the respective apportionment of the total amount of basal insulin medicament between each respective basal injection event type in the one or more periodic injection event types; and
communicating the recommended adjustment to: (i) the subject for manual adjustment of the basal insulin regimen, (ii) an insulin pen charged with delivering the standing basal insulin regimen to the subject, or (iii) a health care practitioner associated with the subject.
17. A computer program comprising instructions that, when executed by one or more processors, perform the method of embodiment 16.
18. A computer-readable data carrier having stored thereon the computer program according to embodiment 17.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIGS. 1, 2, 3, 5 and/or described in FIG. 4. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

The invention claimed is:
1. A device for optimizing basal administration timing in a standing basal insulin regimen for a subject, wherein the device comprises one or more processors and a memory, the memory storing instructions that, when executed by the one or more processors, perform a method of:
obtaining the standing basal insulin regimen for the subject, wherein the standing basal insulin regimen specifies (i) a total amount of basal insulin medicament for a recurring period, (ii) one or more basal injection event types in a set of basal injection event types for the recurring period, and (iii) a respective apportionment of the total amount of basal insulin medicament between each respective basal injection event type in the one or more basal injection event types;
obtaining, in the memory, from a continuous glucose monitor coupled with the subject, communicatively linked to the memory, and configured to continuously and autonomously provide physiological measurements comprising blood glucose of the subject, a first data set, the first data set comprising a plurality of glucose measurements of the subject over a past time course, the past time course comprising a first plurality of instances of the recurring period and, for each respective glucose measurement in the plurality of glucose measurements, a glucose measurement timestamp representing when the respective measurement was made;
evaluating the plurality of glucose measurements over the past time course using a stop condition, wherein, when the stop condition is satisfied, the method further comprises:
determining a recommended adjustment comprising a change in the number of basal injection event types in the standing basal insulin regimen and/or a change in the respective apportionment of the total amount of basal insulin medicament between each respective basal injection event type in the one or more basal injection event types;
communicating the recommended adjustment to:
(i) the subject for manual adjustment of the standing basal insulin regimen,

(ii) the insulin pen charged with delivering the standing basal insulin regimen to the subject, or (iii) a health care practitioner associated with the subject;

applying the recommended adjustment to a next recurring period, and wherein the standing basal insulin regimen specifies a single basal injection event type for the recurring period, and the evaluating the plurality of glucose measurements over the past time course using the stop condition comprises:

obtaining one or more fasting events in the past time course, wherein each fasting event is associated with a different instance of the recurring period in the first plurality of instances of the recurring period, comparing, for each respective fasting event in the one or more fasting events, (i) one or more first glucose measurements of the subject in the first data set occurring at a first time slot that is a first predetermined amount of time prior to a beginning of the respective fasting event to (ii) one or more second glucose measurements of the subject in the first data set occurring at a second time slot that is at a predetermined point within or after the respective fasting event, thereby obtaining one or more comparisons, wherein, the stop condition is satisfied when the one or more comparisons indicate that the respective one or more first glucose measurements deviate from the corresponding respective one or more second glucose measurements by more than a threshold amount, and the recommended adjustment is to increase the number of basal injection event types to two basal injection event types and to apportion the total amount of basal insulin medicament between the two basal injection event types.

2. The device of claim 1, wherein the standing basal insulin regimen specifies a single basal injection event type for the recurring period, and the evaluating the plurality of glucose measurements over the past time course using the stop condition comprises:

obtaining a plurality of fasting events in the past time course, wherein each fasting event is associated with a different instance of the recurring period in the first plurality of instances of the recurring period, obtaining, for each respective fasting event in the plurality of fasting events, (i) a first glucose measurements of the subject in the first data set occurring at a first time slot that is a first predetermined amount of time prior to a beginning of the respective fasting, and (ii) a second glucose measurements of the subject in the first data set occurring at a second time slot that is at a predetermined point within or after the respective fasting event, obtaining a first measure of central tendency of the first glucose measurement of each fasting event in the plurality of fasting event, and a second measure of central tendency of the second glucose measurement of each fasting in the plurality of fasting events, and comparing the first measure of central tendency to the second measure of central tendency, and thereby obtaining a comparison, wherein, the stop condition is satisfied when the comparison indicate that the respective first measure of central tendency deviate from the second measure of central tendency by more than a threshold amount, and the recommended adjustment is to increase the number of basal injection event types to two basal injection event types and to apportion the total amount of basal insulin medicament between the two basal injection event types.

3. The device of claim 1, wherein the obtaining the one or more fasting events comprises identifying a first fasting event in a first recurring period in the first plurality of recurring periods by computing a moving period of variance $\sigma_k^2$ across the plurality of glucose measurements, wherein:

$$\sigma_k^2 = \left(\frac{1}{M}\sum_{i=k-M+1}^{k}(G_i - \bar{G})\right)^2$$

wherein, $G_i$ is the $i^{th}$ glucose measurement in a portion k of the plurality of glucose measurements, M is a number of glucose measurements in the plurality of glucose measurements and represents the past time course, $\bar{G}$ is the mean of the glucose measurements selected from the plurality of glucose measurements, and k is within the first recurring period; and associating the first fasting event with a region of minimum variance $$\min_k \sigma_k^2$$

within the first recurring period.

4. The device of claim 1, wherein the obtaining the one or more fasting events comprises receiving an indication of each fasting event in the one or more fasting events from the subject.

5. The device of claim 1, wherein the obtaining the one or more fasting events comprises receiving a second data set from a wearable device worn by the subject, and the second data set indicates a physiological metric of the subject during the past time course that is indicative of the one or more fasting events.

6. The device of claim 1, the method further comprising:

obtaining a third data set from an insulin pen used by the subject to apply the standing basal insulin regimen, the third data set comprising a plurality of insulin medicament records, each respective insulin medicament record in the plurality of medicament records comprising: (i) a respective insulin medicament injection event including an amount of basal insulin medicament injected into the subject and (ii) a corresponding insulin event electronic timestamp that is automatically generated by the insulin pen upon occurrence of the respective insulin medicament injection event, and using the third data set and the standing basal insulin regimen to determine one or more recurring periods in the past time course that do not comply with the standing basal insulin regimen for the subject; and excluding from the stop condition evaluation those glucose measurements in the one or more recurring periods in the past time course that do not comply with the standing basal insulin regimen.

7. The device of claim 1, wherein
the set of basal injection event types for the recurring period consists of "morning basal," and "night basal,"
the standing basal insulin regimen specifies a single basal injection event type for the recurring period of "morning basal," and
the recommended adjustment is to add the "night basal" basal injection event type to the standing basal insulin regimen and to apportion the total amount of basal insulin medicament between the "night basal" basal injection event type and the "morning basal" basal injection event type.

8. The device of claim 1, wherein the method further comprises:
obtaining a second data set from an insulin pen used by the subject to apply the standing basal insulin regimen, the second data set comprising a plurality of insulin medicament records over the past time course, each insulin medicament record in the plurality of medicament records comprising:
(i) a respective insulin medicament injection event representing an insulin medicament injection of the basal insulin medicament into the subject using the insulin pen and
(ii) a corresponding electronic timestamp that is automatically generated by the insulin pen upon occurrence of the respective insulin medicament injection event; and
using the first data set and the second data set to simulate a glucose concentration of the subject over a future time course a plurality of times, thereby computing a plurality of simulations of the glucose concentration of the subject over the future time course, wherein
each respective simulation in the plurality of simulations is associated with a different apportionment of the total amount of basal insulin medicament across the set of basal injection event types,
the evaluating the plurality of glucose measurements over the past time course using the stop condition comprises evaluating the glucose concentration of the subject across the future time course in each respective simulation in the plurality of simulations by calculating a glycaemic risk metric for each simulation,
the stop condition is satisfied when a first simulation in the plurality of simulations minimizes the glycaemic risk metric, by more than a threshold amount as compared to one of:
(i) a reference simulation of the glucose concentration of the subject over the future time course based upon the apportionment of the total amount of basal insulin medicament across the set of basal injection event types specified in the standing basal insulin regimen and
(ii) the glucose concentration of the subject across the first data set, and
the apportionment of the total amount of basal insulin medicament across the set of basal injection event types in the first simulation is different than that of the standing basal insulin regimen.

9. The device of claim 8, wherein the glycaemic risk metric comprises:
(i) a total glucose level variability observed across the respective simulation,
(ii) a variability in a plurality of fasting glucose levels calculated across the respective simulation,
(iii) a percentage of time that a total glucose level exceeds a first threshold value or falls below a second threshold value across the respective simulation, or
(iv) a percentage of time that an HbA1c level exceeds a third threshold value or falls below a fourth threshold value across the respective simulation.

10. The device of claim 8, the method further comprising:
obtaining a meal record data set comprising a plurality of meal records over the past time course for the subject, each respective meal record in the meal record data set comprising: (i) a carbohydrate intake event and (ii) a corresponding electronic carbohydrate timestamp of when the carbohydrate intake event occurred; and wherein
the using the first data set and the second data set to simulate a glucose concentration of the subject over a future time course a plurality of times comprises using the first data set, the second data set, and the meal record data set to simulate a glucose concentration of the subject over the future time course the plurality of times.

11. The device of claim 10, the method further comprising:
obtaining a fourth data set comprising physical exertion of the subject over the past time course and wherein
the using the first data set and the second data set to simulate a glucose concentration of the subject over a future time course a plurality of times comprises using the first data set, the second data set, the third data set and the fourth data set to simulate a glucose concentration of the subject over the future time course the plurality of times.

12. The device of claim 1, wherein
the set of basal injection event types for the recurring period consists of "morning basal" and "night basal," and
the recurring period is a day.

13. The device of claim 1, wherein successive measurements in the plurality of glucose measurements in the first data set are autonomously taken from the subject at an interval rate of 5 minutes or less, 3 minutes or less, or 1 minute or less.

14. The device of claim 1, wherein
the past time course is the last week, the last two weeks, or the last month and wherein the method is repeated on a recurring basis over time, and
the basal insulin medicament consists of a single insulin medicament having a duration of action that is between 12 and 24 hours or a mixture of insulin medicaments that collectively have a duration of action that is between 12 and 24 hours.

15. A method for optimizing basal administration timing in a standing basal insulin regimen for a subject, the method comprising:
obtaining the standing basal insulin regimen for the subject, wherein the standing basal insulin regimen specifies (i) a total amount of basal insulin medicament for a recurring period, (ii) one or more basal injection event types in a set of basal injection event types for the recurring period, and (iii) a respective apportionment of the total amount of basal insulin medicament between each respective basal injection event type in the one or more basal injection event types;
obtaining, in a memory, from a continuous glucose monitor coupled with the subject, communicatively linked to the memory, and configured to continuously and autonomously provide physiological measurements comprising blood glucose of the subject, a first data set, the first data set comprising a plurality of glucose measurements of the subject over a past time course, the past time course comprising a first plurality of instances of the recurring period and, for each respective glucose measurement in the plurality of glucose measurements, a timestamp representing when the respective measurement was made;

evaluating the plurality of glucose measurements over the past time course using a stop condition, wherein, when the stop condition is satisfied, the method further comprises:

determining a recommended adjustment comprising a change in the number of basal injection event types in the standing basal insulin regimen and/or a change in the respective apportionment of the total amount of basal insulin medicament between each respective basal injection event type in the one or more periodic injection event types;

communicating the recommended adjustment to:
  (i) the subject for manual adjustment of the basal insulin regimen,
  (ii) an insulin pen charged with delivering the standing basal insulin regimen to the subject, or
  (iii) a health care practitioner associated with the subject;

applying the recommended adjustment to a next recurring period, and wherein the standing basal insulin regimen specifies a single basal injection event type for the recurring period, and the evaluating the plurality of glucose measurements over the past time course using the stop condition comprises:
  obtaining one or more fasting events in the past time course, wherein each fasting event is associated with a different instance of the recurring period in the first plurality of instances of the recurring period,
  comparing, for each respective fasting event in the one or more fasting events, (i) one or more first glucose measurements of the subject in the first data set occurring at a first time slot that is a first predetermined amount of time prior to a beginning of the respective fasting event to (ii) one or more second glucose measurements of the subject in the first data set occurring at a second time slot that is at a predetermined point within or after the respective fasting event, thereby obtaining one or more comparisons,
  wherein, the stop condition is satisfied when the one or more comparisons indicate that the respective one or more first glucose measurements deviate from the corresponding respective one or more second glucose measurements by more than a threshold amount, and
  the recommended adjustment is to increase the number of basal injection event types to two basal injection event types and to apportion the total amount of basal insulin medicament between the two basal injection event types.

16. A non-transitory computer-readable data carrier having stored thereon computer program code that, when executed, causes a computer to perform steps of optimizing basal administration timing in a standing basal insulin regimen for a subject, comprising:

obtaining the standing basal insulin regimen for the subject, wherein the standing basal insulin regimen specifies (i) a total amount of basal insulin medicament for a recurring period, (ii) one or more basal injection event types in a set of basal injection event types for the recurring period, and (iii) a respective apportionment of the total amount of basal insulin medicament between each respective basal injection event type in the one or more basal injection event types;

obtaining, in a memory, from a continuous glucose monitor coupled with the subject, communicatively linked to the memory, and configured to continuously and autonomously provide physiological measurements comprising blood glucose of the subject, a first data set, the first data set comprising a plurality of glucose measurements of the subject over a past time course, the past time course comprising a first plurality of instances of the recurring period and, for each respective glucose measurement in the plurality of glucose measurements, a timestamp representing when the respective measurement was made;

evaluating the plurality of glucose measurements over the past time course using a stop condition, wherein, when the stop condition is satisfied, the method further comprises:

determining a recommended adjustment comprising a change in the number of basal injection event types in the standing basal insulin regimen and/or a change in the respective apportionment of the total amount of basal insulin medicament between each respective basal injection event type in the one or more periodic injection event types; and communicating the recommended adjustment to:
  (i) the subject for manual adjustment of the basal insulin regimen,
  (ii) an insulin pen charged with delivering the standing basal insulin regimen to the subject, or
  (iii) a health care practitioner associated with the subject;

applying the recommended adjustment to a next recurring period, and wherein the standing basal insulin regimen specifies a single basal injection event type for the recurring period, and the evaluating the plurality of glucose measurements over the past time course using the stop condition comprises:
  obtaining one or more fasting events in the past time course, wherein each fasting event is associated with a different instance of the recurring period in the first plurality of instances of the recurring period,
  comparing, for each respective fasting event in the one or more fasting events, (i) one or more first glucose measurements of the subject in the first data set occurring at a first time slot that is a first predetermined amount of time prior to a beginning of the respective fasting event to (ii) one or more second glucose measurements of the subject in the first data set occurring at a second time slot that is at a predetermined point within or after the respective fasting event, thereby obtaining one or more comparisons,
  wherein, the stop condition is satisfied when the one or more comparisons indicate that the respective one or more first glucose measurements deviate from the corresponding respective one or more second glucose measurements by more than a threshold amount, and
  the recommended adjustment is to increase the number of basal injection event types to two basal injection event types and to apportion the total amount of basal insulin medicament between the two basal injection event types.

* * * * *